United States Patent
Peng et al.

(10) Patent No.: US 9,182,350 B2
(45) Date of Patent: Nov. 10, 2015

(54) NAPHTHALENE-BASED TWO-PHOTON FLUORESCENT PROBES, PREPARATION METHOD AND USE THEREOF

(75) Inventors: Xiaojun Peng, Liaoning (CN); Hua Zhang, Liaoning (CN); Jiangli Fan, Liaoning (CN); Jingyun Wang, Liaoning (CN)

(73) Assignees: DALIAN UNIVERSITY OF TECHNOLOGY, Dalian, Liaoning (CN); DALIAN CHROMAS BIOSCIENCE CO., LTD., Dalian, Liaoning (CN)

( * ) Notice: Subject to any disclaimer, the term of this patent is extended or adjusted under 35 U.S.C. 154(b) by 0 days.

(21) Appl. No.: 14/383,000

(22) PCT Filed: Mar. 5, 2012

(86) PCT No.: PCT/CN2012/071940
§ 371 (c)(1),
(2), (4) Date: Sep. 4, 2014

(87) PCT Pub. No.: WO2013/131235
PCT Pub. Date: Sep. 12, 2013

(65) Prior Publication Data
US 2015/0079625 A1    Mar. 19, 2015

(51) Int. Cl.
C07D 403/12 (2006.01)
G01N 21/64 (2006.01)
C07D 401/12 (2006.01)
C07D 471/04 (2006.01)
C09K 11/02 (2006.01)
G01N 33/58 (2006.01)
C07D 471/06 (2006.01)

(52) U.S. Cl.
CPC .......... *G01N 21/6486* (2013.01); *C07D 401/12* (2013.01); *C07D 403/12* (2013.01); *C07D 471/04* (2013.01); *C07D 471/06* (2013.01); *C09K 11/02* (2013.01); *G01N 21/6458* (2013.01); *G01N 33/582* (2013.01); *C09K 2211/1007* (2013.01); *C09K 2211/1029* (2013.01); *C09K 2211/1044* (2013.01); *G01N 2201/0697* (2013.01); *G01N 2201/06113* (2013.01)

(58) Field of Classification Search
CPC ..................................................... C07D 403/12
USPC .................................................. 548/454, 455
See application file for complete search history.

(56) References Cited

FOREIGN PATENT DOCUMENTS

| | | |
|---|---|---|
| CN | 1896074 A | 1/2007 |
| CN | 101786985 A | 7/2010 |

*Primary Examiner* — Shawquia Jackson
(74) *Attorney, Agent, or Firm* — Novick, Kim & Lee, PLLC; Allen Xue

(57) ABSTRACT

The present invention provides a novel category of naphthalene-based two-photon fluorescent probes having a general formula I, wherein: X is selected from the $X_1$, $X_2$, $X_3$ and $X_4$; The mentioned two-photon fluorescent probes have a low fluorescence background in the non-tumor cells and tissues, and have a strong and specific fluorescent signal in the tumor cells and tissues. These probes have a certain level of water-solubility, while having good membrane permeability. In addition, they have a bigger effective two-photon absorption cross section. The compounds of the present invention also have a lower biotoxicity, phototoxicity and photobleaching. There is sufficient difference between the spectral range thereof and that of a biological sample.

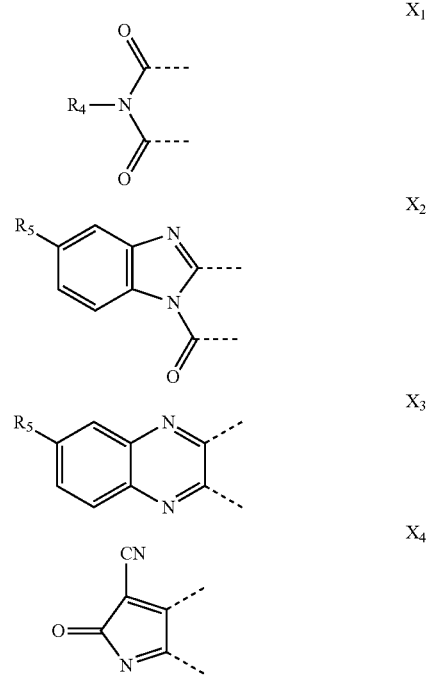

10 Claims, 7 Drawing Sheets

I a b

NAPHTHALENE-BASED TWO-PHOTON FLUORESCENT PROBES, PREPARATION METHOD AND USE THEREOF

FIELD OF THE INVENTION

The present invention relates to a novel category of naphthalene-based two-photon fluorescent probes, their synthesizing methods and a method of utilizing the naphthalene-based two-photon fluorescent probes to label the tumor cells or tissues.

BACKGROUND OF THE INVENTION

Currently, the cancer rates are greatly increased and are in a "blowout". The WHO international cancer research center has announced a "world cancer report" said, according to the current trend of cancer, in 2020, the world cancer rates will increase 50% than now, global new cancer cases every year there well be up to 15 million people. Thus, to develop a simple, rapid, sensitive and effective method for cancer labeling is becoming more and more urgent. At present, methods for cancer labeling are X-ray detection technology, ultrasonic technology, CT detection technology, magnetic resonance (MRI) testing technology, infrared thermal image detection technology, near infrared scan detection technology, PET-CT detection technology and so on. However, the above-mentioned methods have the following disadvantages in practical imaging applications: lack of specificity for imaging, with large radiation damage, cannot diagnose the cancer by independent labeling, unable to deep imaging for tumors and so on. The optical molecular imaging fluorescence labeling technique overcomes latter's problems of these methods mentioned above. The relevant commercial fluorescent dyes, such as phenanthridine derivative (EB, PI), acridine (AO), imidazoles (Hoechst, DAPI), cyanine dyes (Cy, TOTO, SYTO) and so on, play an important role in the areas of the genomics technology, nucleic acid quantitative testing and blood cell analysis. However, the fluorescent dyes/probes for specific cancer labeling are lacking.

In recent years, with the development of two-photon technique, the two-photon fluorescence microscope has become most important imaging tools in the study of life sciences. Compared with single-photon fluorescence confocal microscope, the two-photon fluorescence microscope has significant advantages, including near-infrared excitation, dark-field imaging, reduced photodamage and photobleaching, high lateral resolution and vertical resolution, reduced absorption coefficient of biological tissues, so on. (Helmchen F, Svoboda K, Denk W et al. Nature, 1999, 2:989-996. Maiti S, Shear J B, Williams R M et al. Science, 1997, 275:530. Ventelon L, Charier S, Moreaux L et al. Angewandte Chemie International Edition, 2001, 40: 2098). The two-photon fluorescence imaging technique provides a new platform for biological imaging. Regrettably, two-photon fluorescence probes for the imaging of tumor in vivo are rarely reported. So, exploring novel two-photon fluorescence probes having a good labeling specificity for cancer is the key to achieve two-photon imaging of tumors.

SUMMARY OF THE INVENTION

The present invention provides a novel category of naphthalene-based two-photon fluorescent probes of formula I:

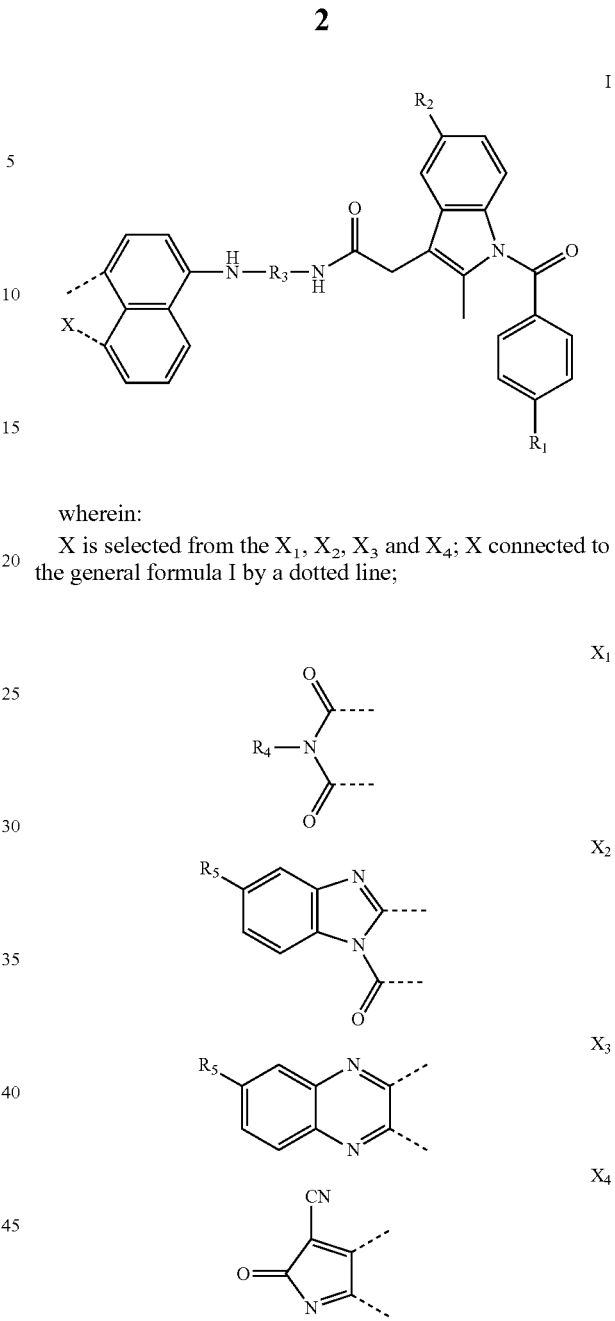

wherein:

X is selected from the $X_1$, $X_2$, $X_3$ and $X_4$; X connected to the general formula I by a dotted line;

$R_1$ and $R_2$ are each independently selected from the group consisting of —$OCH_3$,' —$OCOCH_3$ and halogen;

$R_3$ is selected from the group consisting of —$CH_2$—, —$(CH_2)_2$—, —$(CH_2)_3$—, —$(CH_2)_4$—, —$(CH_2)_5$—, —$(CH_2)_6$—, —$(CH_2)_7$— and —$(CH_2)_8$—;

$R_4$ is selected from the group consisting of $C_{1-6}$ alkyl, $HOCH_2$—, $HO(CH_2)_2$—, $HO(CH_2)_3$—, $HO(CH_2)_4$—, $HO(CH_2)_5$— and $HO(CH_2)_6$—;

$R_5$ is selected from the group consisting of —H, —CN, —COOH, —$NH_2$, —$NO_2$, —OH and —SH;

In another aspect, the present invention further provides a method for synthesizing the above-mentioned compounds of Formula I which includes the following steps:

1) synthesizing the compound V by reacting the 4-Bromo-1,8-naphthalic anhydride with $R_4$—$NH_3$ in a mole ratio of 1:1-1:5;

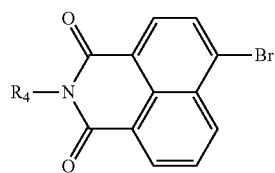

the reaction temperature is 70-150° C.; the reaction time is 1-12 hours; the reaction solvent is dichloromethane, ethanol, ethyl acetate, acetic acid or their mixture;

2) synthesizing the compound VI by reacting the 4-Bromo-1,8-naphthalic anhydride with compound i in a mole ratio of 1:1-1:5;

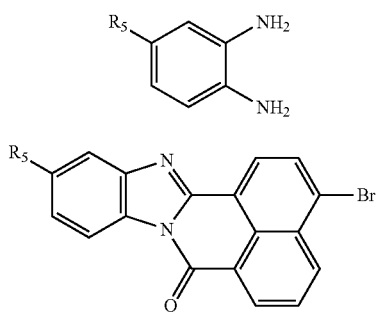

the reaction temperature is 70-150° C.; the reaction time is 1-12 hours; the reaction solvent is dichloromethane, ethanol, ethyl acetate, acetic acid or their mixture;

3) synthesizing the compound VII by reacting the 4-bromoacenaphthenequinone with compound i in a mole ratio of 1:1-1:5;

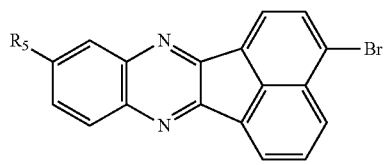

the reaction temperature is 70-150° C.; the reaction time is 1-12 hours; the reaction solvent is dichloromethane, ethanol, ethyl acetate, acetic acid or their mixture;

4) synthesizing the compound VIII by reacting acenaphthenequinone with malononitrile and dimethyl sulfoxide in a mole ratio of 1:1:5;

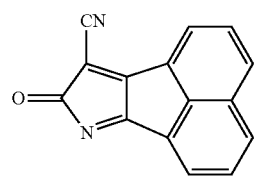

after the reaction processed at room temperature for 0.5 hours, the reaction temperature increased to 70-180° C., and the reaction continued for 4-12 hours; the reaction solvent is dimethyl sulfoxide, tetrahydrofuran or their mixture with water;

5) synthesizing the compounds IX, X, XI and XII by reacting the $NH_2R_3NH_2$ with compound V, VI, VII and VIII respectively in a mole ratio of 1:1-1:2.5;

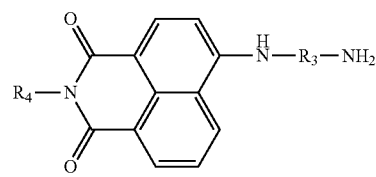

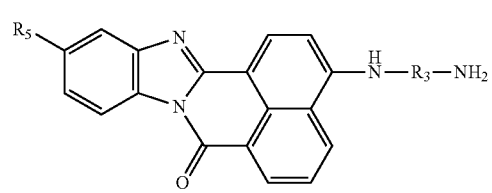

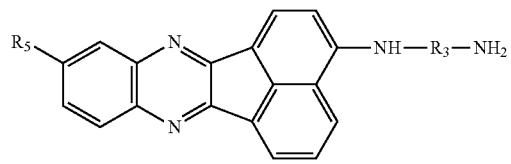

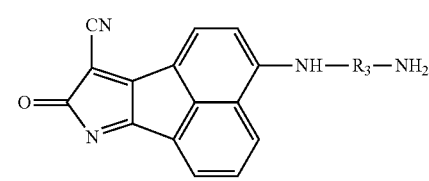

the reaction temperature is 100-175° C.; the reaction time is 1-7 hours; the reaction solvent is selected from ethanol, ethylene glycol monomethyl ether or their mixture;

6) synthesizing the compounds of formula I was obtained by reacting the compound ii with compound IX, X, XI and XII respectively in a mole ratio of 1:1-1:3;

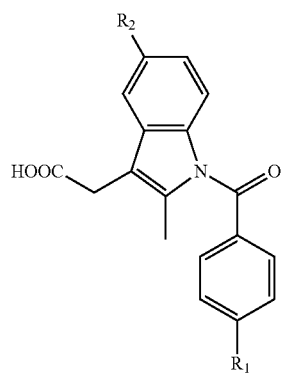

-continued

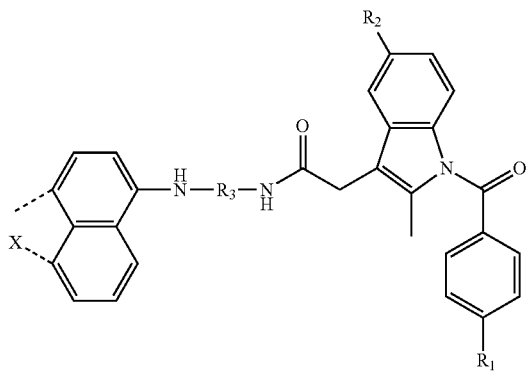

I the reaction temperature is 0-100° C.; the reaction time is 12-48 hours; the reaction solvent is methylene chloride, ethanol, ethyl acetate or their mixture; the reaction is progressed in the presence of organic base and the 4-dimethyl amino pyridine was used as catalyzer.

In the description of synthesizing methods for naphthalene-based two-photon fluorescence probes, the definition of each substituent, that is, $R_1$, $R_2$, $R_3$, $R_4$ and $R_5$, are same as the definition mentioned above.

On the other hand, present invention provides a method for labeling biological samples utilizing the naphthalene-based two-photon fluorescent probes mentioned above, especially, for the labeling of tumor cells and tissues.

To overcome existing problems, a class of two-photon fluorescent dyes for effective and specific labeling the living tumor cells and tissues were designed and synthesized in this invention. The two-photon fluorescent dyes have a low fluorescence background in the non-tumor cells and tissues, and have a strong and specific fluorescent signal in the tumor cells and tissues. These compounds have a certain level of water-solubility, while having good membrane permeability. In addition, they have a bigger effective two-photon absorption cross section. The compounds of the present invention also have a lower biotoxicity, phototoxicity and photobleaching. There is sufficient difference between the spectral range thereof and that of a biological sample.

BRIEF DESCRIPTION OF THE DRAWINGS

There are 13 drawings in this invention:

FIG. 2 (a) is confocal image of Hela cell, FIG. 2 (b) is confocal image of HEK293 cell.

FIG. 4 (a) is confocal image of Hela cell, FIG. 4 (b) is confocal image of HEK293 cell.

FIG. 8 (a1) and (a2) are the confocal images of tumor tissue sections of mice' lungs after adding probe $A_4$, FIG. 8 (b1) and (b2) are the confocal images of non-tumor tissue sections of mice' lungs after adding probe $A_4$. The images of FIG. 8 (a1) and (b1) were recorded with the emission in the range of 500-550 nm. The images of FIG. 8 (a2) and (b2) were recorded with the emission in the range of 570-650 nm.

FIG. 10 (a1) and (a2) are confocal image of Hela cell, FIG. 10 (b1) and 10(b1) are confocal image of HEK293 cell. The images of FIG. 10 (a1) and (b1) were recorded with the emission in the range of 500-550 nm. The images of FIG. 10 (a2) and (b2) were recorded with the emission in the range of 570-650 nm.

FIG. 11 (a1) and (a2) are the confocal images of tumor tissue sections of mice' lungs, FIG. 11 (b1) and (b2) are the confocal images of non-tumor tissue sections of mice' lungs. The images of FIG. 11 (a1) and (b1) were recorded with the emission in the range of 500-550 nm. The images of FIG. 11 (a2) and (b2) were recorded with the emission in the range of 570-650 nm.

DETAILED DESCRIPTION OF PREFERRED EMBODIMENTS

Figure 1:
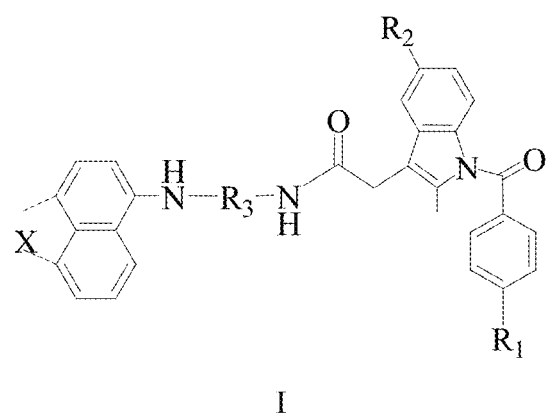
FIG. 1 is the general formula I of naphthalene-based two-photon fluorescence probes in this invention.

Unless otherwise specified, the terms used in this invention have the following meanings:

The term "alkyl" used herein includes straight and branched alkyl groups. In reference to a single alkyl such as "propyl", it specifically means a straight alkyl group, while in reference to a single branched alkyl such as "isopropyl", it specifically means a branched alkyl group. For example, "$C_{1-6}$ alkyl" includes $C_{1-4}$ alkyl, $C_{1-3}$ alkyl, methyl, ethyl, n-propyl, isopropyl and tert-butyl. The similar rule applies to other groups used in this invention.

The term "halogen" used herein includes fluorine, chlorine, bromine and iodine.

The compounds of formula I in this invention, preferably $R_1$ and $R_2$ are each independently selected from the group consisting of —$OCH_3$', —$OCOCH_3$ and halogen, more preferably $R_1$ and $R_2$ are independently selected from the group consisting of —$OCH_3$ and halogen, even more preferably, $R_1$ and $R_2$ are independently selected from the group consisting of —$OCH_3$ and —Cl, most preferably $R_1$ is —$OCH_3$, $R_2$ is —Cl.

Preferably $R_3$ is —$(CH_2)_{3-7}$—, more preferably $R_3$ is selected from —$(CH_2)_5$— and —$(CH_2)_6$—.

Preferably $R_4$ is selected from the group consisting of $C_{1-6}$ alkyl, $HOCH_2$—, $HO(CH_2)_2$—, $HO(CH_2)_3$—, $HO(CH_2)_4$—, $HO(CH_2)_5$— and $HO(CH_2)_6$—, more preferably $R_4$ is $C_{1-6}$ alkyl, most preferably $R_4$ is $C_{1-4}$ alkyl;

Preferably $R_5$ is selected from the group consisting of —H, —CN, —COOH, —$NH_2$, —$NO_2$, —OH and —SH, more preferably $R_5$ is selected from the group consisting of —H, —CN, —COOH, —$NH_2$, and —$NO_2$, even more preferably $R_5$ is selected from the group consisting of —H, —CN, —COOH, and —$NO_2$, most preferably $R_5$ is selected from the group consisting of —H and —$NO_2$.

On the other hand, the present invention further provides a method for synthesizing the naphthalene-based two-photon fluorescent probes, which includes the following steps:

1) synthesizing the compound V by reacting the 4-bromo-1,8-naphthaleneic anhydride reacted with $R_4$—$NH_3$ in a mole ratio of 1:1-1:5;

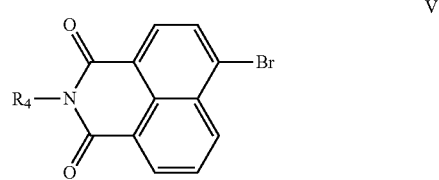

the reaction temperature is 70-150° C.; the reaction time is 1-12 hours, the reaction solvents is dichloromethane, ethanol, ethyl acetate, acetic acid or their mixture;

In the preferred embodiments, the reaction temperature is 80-140° C., the reaction time is 2-10 hours, the reaction solvents is ethanol, ethyl acetate, acetic acid or their mixture, the mole ratio between 4-bromo-1,8-naphthalic anhydride and $R_4$—$NH_3$ is 1:1-1:4;

In the more preferred embodiments, the reaction temperature is 90-120° C., reaction time is 3-10 hours, the reaction solvents is ethyl acetate, acetic acid or their mixture, the mole ratio between 4-bromio-1,8-naphthalic anhydride and $R_4$—$NH_3$ is 1:1-1:3;

In the most preferred embodiments, the reaction temperature is 95-110° C., reaction time is 4-8 hours, the reaction solvents is ethyl acetate, acetic acid or their mixture, the mole ratio between 4-bromo-1,8-naphthalic anhydride and $R_4$—$NH_3$ is 1:1-1:2;

2) synthesizing the compound VI by reacting 4-bromo-1,8-naphthalic anhydride with compound i in a mole ratio of 1:1-1:5;

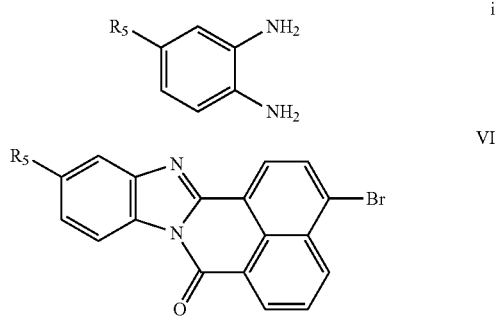

the reaction temperature is 70-150° C., the reaction time is 1-12 hours, the reaction solvents is dichloromethane, ethanol, ethyl acetate, acetic acid or their mixture;

In the preferred embodiments, the reaction temperature is 80-140° C., the reaction time is 2-10 hours, the reaction solvents is ethanol, ethyl acetate, acetic acid or their mixture, the mole ratio between 4-bromo-1,8-naphthalic anhydride and compound i is 1:1-1:4;

In the more preferred embodiments, the reaction temperature is 90-120° C., the reaction time is 3-10 hours, the reaction solvents is ethyl acetate, acetic acid or their mixture, the mole ratio between 4-bromo-1,8-naphthalic anhydride and compound i is 1:1-1:3;

In the most preferred embodiments, the reaction temperature is 95-110° C., the reaction time is 4-8 hours, the reaction solvents is acetic acid, the mole ratio between 4-bromo-1,8-naphthalic anhydride and compound i is 1:1-1:2;

3) synthesizing the compound VII by reacting the 4-bromoacenaphthenequinone with compound i in a mole ratio of 1:1-1:5;

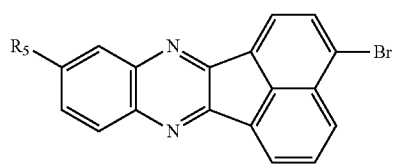

VII the reaction temperature is 70-150° C., the reaction time is 1-12 hours, the reaction solvents is dichloromethane, ethanol, ethyl acetate, acetic acid or their mixture;

In the preferred embodiments, the reaction temperature is 80-140° C., the reaction time is 2-10 hours, the reaction solvents is ethanol, ethyl acetate, acetic acid or their mixture, the mole ratio between 4-bromoacenaphthenequinone and compound i is 1:1-1:4;

In the more preferred embodiments, the reaction temperature is 90-120° C., the reaction time is 3-10 hours, the reaction solvents is ethyl acetate, acetic acid or their mixture, the mole ratio between 4-bromoacenaphthenequinone and compound i is 1:1-1:3;

In the most preferred embodiments, the reaction temperature is 95-110° C., reaction time is 4-8 hours, the reaction solvents is acetic acid, the mole ratio between 4-bromoacenaphthenequinone and compound i is 1:1-1:2;

4) synthesizing the compound VIII by reacting acenaphthenequinone with malononitrile and dimethyl sulfoxide in a mole ratio of 1:1:5;

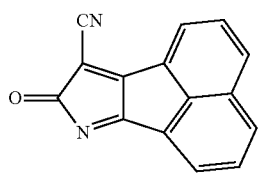

VIII after the reaction processed at room temperature for 0.5 hours, the reaction temperature increased to 70-180° C., and the reaction continued for 4-12 hours; the reaction solvent is dimethyl sulfoxide, tetrahydrofuran, or their mixture with water;

In the preferred embodiments after the reaction processed at room temperature for 0.5 hours, the reaction temperature increased to 80-160° C., and the reaction continued for 4-10 hours; the reaction solvent is dimethyl sulfoxide, tetrahydrofuran, or their mixture with water;

In the more preferred embodiments, after the reaction processed at room temperature for 0.5 hours, the reaction temperature increased to 90-140° C., and the reaction continued for 4-6 hours; the reaction solvent is dimethyl sulfoxide or its mixture with water.

In the most preferred embodiments, after the reaction processed at room temperature for 0.5 hours, the reaction temperature increased to 100-120° C., and the reaction continued for 4-6 hours; the reaction solvent is dimethyl sulfoxide;

5) synthesizing the compounds IX, X, XI and XII by reacting $NH_2R_3NH_2$ with compound V, VI, VII and VIII respectively in a mole ratio 1:1-1:2.5;

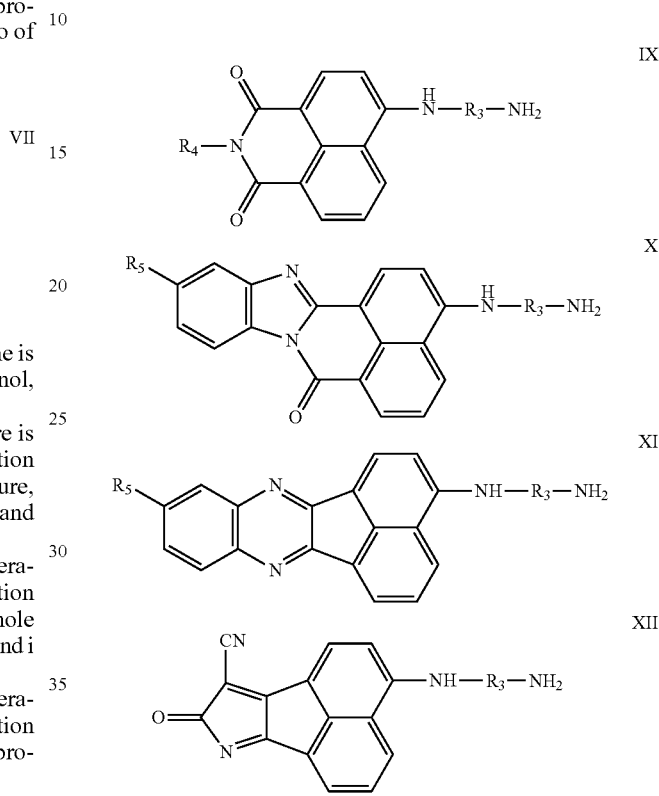

the reaction temperature is 100-175° C., the reaction time is 1-7 hours, the reaction solvents is ethanol, ethylene glycol monomethyl ether or their mixture;

In the preferred embodiments, the reaction temperature is 100-165° C., reaction time is 1-6 hours, the reaction solvents is ethanol, ethylene glycol monomethyl ether or their mixture, the mole ratio between compounds V, VI, VII, VIII and $NH_2R_3NH_2$ is 1:1-1:2.5, respectively;

In the more preferred embodiments, the reaction temperature is 100-150° C., the reaction time is 1-5 hours, the reaction solvents is selected from ethanol, ethylene glycol monomethyl ether or their mixture, the mole ratio between compounds V, VI, VII, VIII and $NH_2R_3NH_2$ is 1:1-1:2, respectively;

In the most preferred embodiments, the reaction temperature is 100-130° C., the reaction time is 1-4 hours, the reaction solvent is ethylene glycol monomethyl ether, the mole ratio between compounds V, VI, VII, VIII and $NH_2R_3NH_2$ is 1:1-1:1.5, respectively;

6) synthesizing the compounds of formula I by reacting compound ii with compound IX, X, XI, XII respectively in a mole ratio of 1:1-1:3;

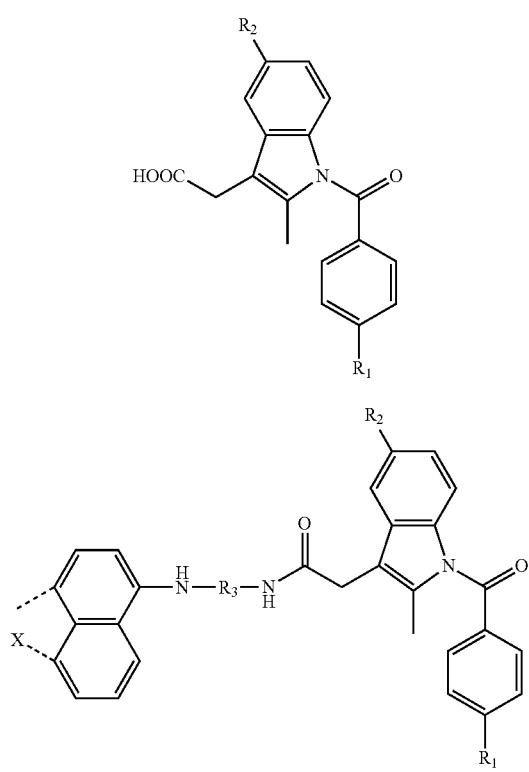

the reaction temperature is 0-100° C., the reaction time is 12-48 hours, the reaction solvent is methylene chloride, ethanol, ethyl acetate or their mixture; the reaction is progressed in the presence of organic base and the 4-dimethyl amino pyridine was used as catalyzer.

In the preferred embodiments, the reaction temperature is 10-80° C., the reaction time is 12-32 hours, the reaction solvent is methylene chloride, ethanol, ethyl acetate or their mixture; the reaction is progressed in the presence of organic base and the 4-dimethyl amino pyridine was used as catalyzer; the mole ratio between compound IX, X, XI or XII and compound ii is 1:1-1:3, respectively;

In the more preferred embodiments, the reaction temperature is 10-70° C., the reaction time is 12-24 hours, the reaction solvent is methylene chloride, ethanol, ethyl acetate or their mixture; the reaction is progressed in the presence of organic base and the 4-dimethyl amino pyridine was used as catalyzer; the mole ratio between compound IX, X, XI or XII and compound ii is 1:1-1:2.5, respectively;

In the most preferred embodiments, the reaction temperature is 10-40° C., the reaction time is 12-24 hours, the reaction solvent is methylene chloride; the reaction is progressed in the presence of organic base and the 4-dimethyl amino pyridine was used as catalyzer; the mole ratio between compound IX, X, XI or XII and compound ii is 1:1-1:1.5, respectively.

The definition and optimization for every substituent group ($R_1'$ $R_2'$ $R_3'$ $R_4$ and $R_5$) in synthesis method for naphthalene-based two-photon fluorescent probes consistent with that for compounds in this invention.

The structures of two-photon fluorescent probe compounds which were synthesized through the above-mentioned methods in this invention, were characterized by NMR spectrometry and Mass spectrometry, and the structures also confirmed with the $^{13}C$-NMR spectrometry and the melting point analysis.

Naphthalene-based two-photon fluorescent probes described in this invention have the following advantages:

Introduction of the specific target point into the molecules of the above-mentioned compounds increases the labeling specificity of new compounds for the tumor cells and tissues. The probes were introduced the specificity target point to improve the specific labeling of tumor cells or tissues.

The compounds described above have excellent two-photon properties, when they used for imaging of biological sample, the compounds have lower light bleaching, light damage and biological toxicity, and the produced fluorescence signal can pentrate deeper into biological tissues;

Emission wavelength of a part of probes was greater than 600 nm, so they can be used for the living imaging;

The compounds containing nitro group can be used as a proportion of the probe to image tumor cells and tissues, which can achieve a good quantitative labeling and avoid the disturbance of external environment factors on the fluorescence intensity;

The compounds described above are low in toxicity and side effects, readily available in raw materials, simple in structure, and suitable for industrialization;

Therefore, the two-photon fluorescent probes described in this invention can be used for the labeling of tumor cells and tissues. The compounds described in this invention can be used directly for labeling the tumor cells and tissues in the form of described herein. Alternatively, the composition containing compounds of this invention can also be used for the labeling tumor cells and tissues. The composition should be included in the effective dose of one of the two-photon fluorescent probe compound in this invention. Furthermore, it also included other components which need in the biological staining, such as, solvent, buffer, and so on. These components are all known in the industry. The above-mentioned composition may exist in the form of aqueous solution, or may exist in other suitable forms of solution by mixing it with water before use.

The present invention further provides a method for the labeling tumor cells and tissues using the two-photon fluorescent probe compounds described above. The method may include the step of contacting the above-mentioned compounds with the biological samples. The term "contacting" used herein may included contacting in solution or solid phase.

The following non-limiting examples may enable one skilled in the field a more complete understanding of the present invention, but not limit the invention in any way.

Example 1

The synthesis of fluorescent probe $A_1$:

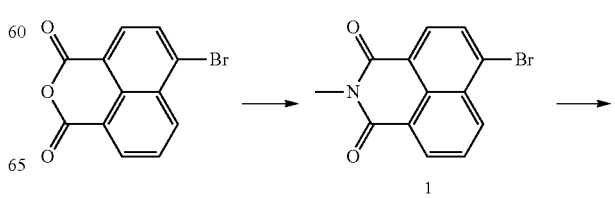

13
-continued

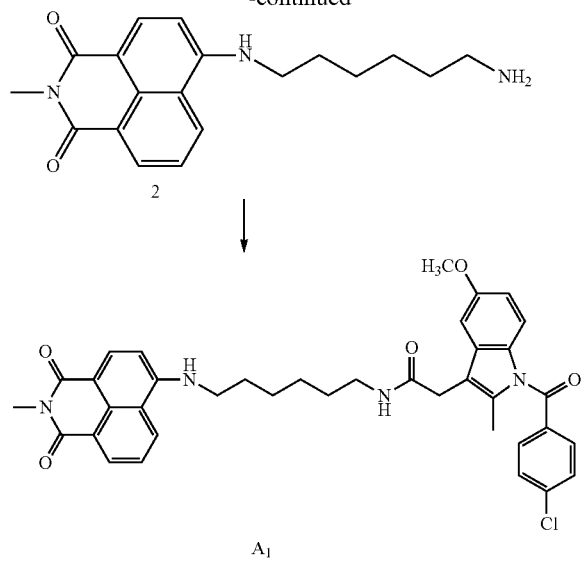

(1) The Synthesis of Intermediate 1:

20 mmol of 4-bromo-1,8-naphthalic anhydride and 25 mmol of methylamine were added into a round-bottom flask containing 10 mL acetic acid under nitrogen protection, the mixture was heated to reflux for 2 h at 100° C. Then the solution was poured into cooled water and filtrated. The white solid powder was collected to obtain the intermediate 1 in a yield of 96%.

(2) The Synthesis of Intermediate 2:

20 mmol of intermediate 1 and 30 mmol of hexamethylenediamine were added into a round-bottom flask containing 20 ml ethylene glycol monomethylether under nitrogen protection, the mixture was heated to reflux for 5 h at 125° C., then the solution was poured into cooled water and filtrated. The residue was collected and purified by silica gel column chromatography, affording the intermediate 2 as a yellow solid powder in a yield of 55%.

(3) The Synthesis of $A_1$ 20 mmol intermediate 2, 25 mmol indomethacin, and 25 mmol 1-(3-dimethylaminopropyl)-3-ethylcarbodiimide (EDC) and small amount of 4-methylpyridine were added into in anhydrous methylene chloride and the mixture was stirred at room temperature under nitrogen protection for 24 h. The solvent was removed by vacuum distillation and the residue was purified by silica gel column chromatography to give a pale-yellow product in a yield of 84%. $^1$H NMR: (400 MHz, DMSO) δ 8.69 (d, J=8.3 Hz, 1H), 8.43 (d, J=7.2 Hz, 1H), 8.25 (d, J=8.5 Hz, 1H), 8.03 (s, 1H), 7.72 (d, J=3.5 Hz, 2H), 7.64 (dt, J=20.8, 6.4 Hz, 5H), 7.12 (d, J=2.4 Hz, 1H), 6.91 (d, J=9.0 Hz, 1H), 6.72 (d, J=8.6 Hz, 1H), 6.68 (dd, J=9.0, 2.5 Hz, 1H), 4.22 (s, 1H), 3.74 (s, 3H), 3.48 (s, 2H), 3.37–3.12 (m, 16H), 3.08 (d, J=6.1 Hz, 2H), 2.51 (d, J=1.6 Hz, 6H), 2.22 (s, 3H), 1.71–1.57 (m, 3H), 1.37 (ddd, J=24.7, 14.6, 6.8 Hz, 8H), 1.23 (s, 1H)o

14

Example 2

Figure 2:
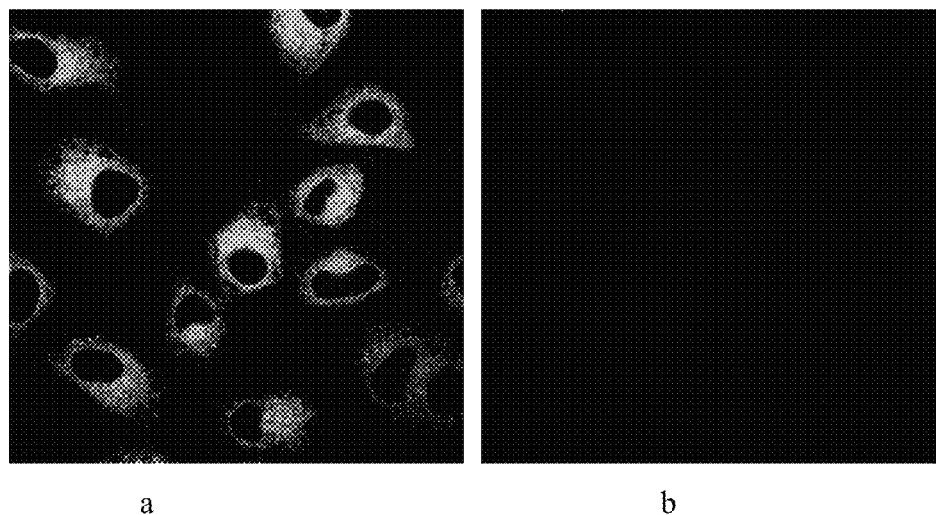
FIG. 2 is the two-photon fluorescent imaging of fluorescent probe compound $A_1$ in the tumor cells and non-tumor cells in example 2. Hela cells and HEK293 cells were incubated with 4 μL of $A_1$-DMSO (4.0 μM) for 60 min in 5% $CO_2$ at 37° C. The representative areas were selected and imaged with oil-immersion objective lens (100×). The resulting images are representative of replicate experiments (n=3). The images were recorded with the emission in the range of 500-550 nm.

The Labeling Experiment of Probe Compound $A_1$ for Cancer Cells and Non-Cancer Cells Compound $A_1$ was used, which was synthesized in the example 1. 4 μL of compound $A_1$-DMSO solution (4 μM) was added into HeLa and HEK 293 cells, respectively. HeLa and HEK 293 cells with probe $A_1$ were cultured for 60 min in 5% $CO_2$ at 37° C. Then, they were washed with phosphate-buffered saline 5 min×3. After that, the fresh medium was added into every cell. The fluorescence imaging was obtained with a two-photon spectral confocal multiphoton microscope. The representative areas were selected and imaged three times with oil-immersion objective lens (100×). The imaging results indicated that there were strong fluorescence signals in HeLa cells, but there were no any fluorescence signal in HEK 293 cells. FIG. 2(a) is confocal image of HeLa cell after adding probe $A_1$, FIG. 2(b) is confocal image of HEK 293 cell after adding probe $A_1$. The images were recorded with the emission in the range of 500-550 nm.

Example 3

The Detection Experiment of the Effective Two-Photon Cross Section (δ) of $A_1$

The two-photon cross section (δ) was determined by the femtosecond two-photon induced fluorescence method The compound $A_1$, which was synthesized in the example 1, was dissolved in methanol, ethanol, acetone, acetonitrile, dioxane, dimethyl sulfoxide, tetrahydrofuran, N,N-dimethyl formamide, water and so on, respectively, at concentration of $1.0 \times 10^{-4}$ M and then the two-photon cross section (δ) was measured by using fluorescein-sodium hydroxide solution (pH=11) as reference solution. The calculated equation was as follow:

$$\delta_s = \delta_r \frac{C_r}{C_s} \frac{n_r}{n_s} \frac{F_s}{F_r} \frac{\Phi_r}{\Phi_s}$$

In this equation, the concentration of solutions was denoted as c, the refractive index was denoted as n which was found in common data table. The upconversion fluorescence intensity was denoted as F, which was obtained by experiment. δ is the two-photon cross section. The reference solution was subscripted r.

Figure 3:
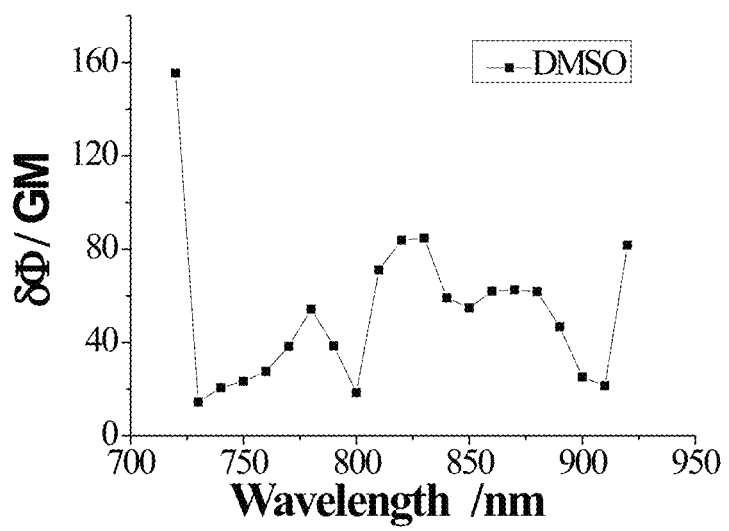
FIG. 3 is the measurement result of two-photon cross section of fluorescent probe compound $A_1$ in different solvents in example 3. The determination solvent is dimethyl sulfoxide (DMSO). The method for determine the two-photon cross section (δ) is femtosecond (fs) fluorescence measurement technique. The reference solution is fluorescein-sodium hydroxide solution (pH=11), the concentration of $A_1$ solutions were $1 \times 10^{-4}$ M, the width of laser pulse is 70 fs, repetition frequency is 80 MHz, the average output power is 1.5 W (780 nm), tunable wavelength range is at 700-980 nm, the wavelength of laser was adjusted to the need wavelength in the experiment.

The effective two-photon cross section (δΦ) in different solution and at different wavelength was detected in FIG. 3. The excitation source of two-photon fluorescence spectra is a mode-locked titanium-sapphire laser, the width of laser pulse is 70 fs, repetition frequency is 80 MHz, the average output power is 1.5 W (780 nm), tunable wavelength range is at 700-980 nm, the wavelength of laser was adjusted to the need wavelength in the experiment.

Example 4

The synthesis of fluorescent probe $A_2$

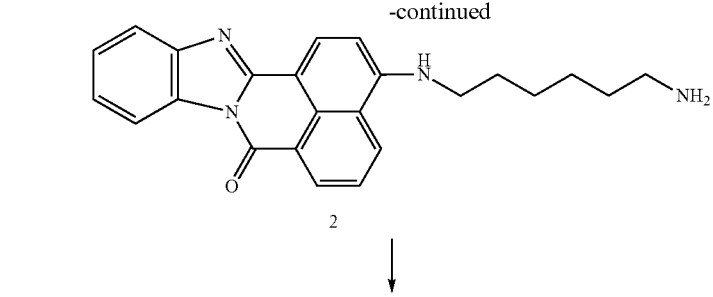

2

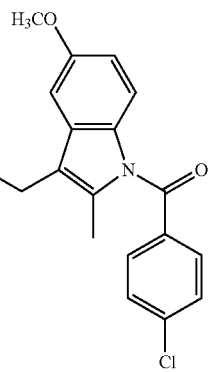

A₂

(1) The Synthesis of Intermediate 1:

20 mmol of 4-bromo-1,8-naphthalic anhydride and 25 mmol of o-phenylenediamine were added into a round-bottom flask containing 10 mL acetic acid under nitrogen protection, the mixture was heated to reflux for 4 h at 95° C. Then the solution was poured into cooled water and filtrated. The yellow solid powder was collected to obtain the intermediate 2 in a yield of 90%.

(2) The Synthesis of Intermediate 2:

20 mmol of intermediate 1 and 25 mmol of hexamethylenediamine were added into a round-bottom flask containing 20 ml ethylene glycol monomethylether under nitrogen protection, the mixture was heated to reflux for 5 h at 125° C., then the solution was poured into cooled water and filtrated. The residue was collected and purified by silica gel column chromatography, affording intermediate 2 as a yellow solid powder in a yield of 63%.

(3) The Synthesis of A₂

20 mmol of intermediate 2, 25 mmol of indomethacin and 25 mmol of 1-(3-dimethylaminopropyl)-3-ethylcarbodiimide (EDC), and small amount of 4-methylpyridine were added into in anhydrous methylene chloride and the mixture was stirred at room temperature for 24 h. The solvent was removed by vacuum distillation and the residue was purified by silica gel column chromatography to give a deep-yellow product $A_2$ in a yield of 84%. $^1$H NMR (400 MHz, DMSO) δ 8.99 (d, J=7.2 Hz, 2H), 8.69 (d, J=8.3 Hz, 1H), 8.43 (d, J=7.2 Hz, 1H), 8.25 (d, J=8.5 Hz, 1H), 8.19 (d, J=6.3 Hz, 2H), 8.03 (s, 1H), 7.85 (d, J=4.6 Hz, 1H), 7.72 (d, J=3.5 Hz, 2H), 7.64 (dt, J=20.8, 6.4 Hz, 5H), 7.12 (d, J=2.4 Hz, 1H), 6.91 (d, J=9.0 Hz, 1H), 6.72 (d, J=8.6 Hz, 1H), 6.68 (dd, J=9.0, 2.5 Hz, 1H), 4.22 (s, 1H), 3.48 (s, 2H), 3.37–3.12 (m, 16H), 3.08 (d, J=6.1 Hz, 2H), 2.51 (d, J=1.6 Hz, 6H), 2.22 (s, 3H), 1.71–1.57 (m, 3H), 1.37 (ddd, J=24.7, 14.6, 6.8 Hz, 8H), 1.23 (s, 1H)○

Example 5

Figure 4:
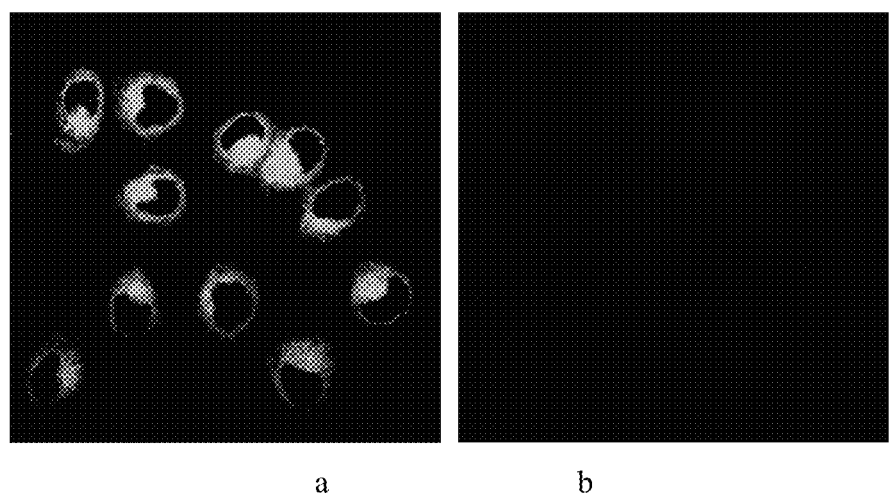
FIG. 4 is the two-photon fluorescent imaging of fluorescent probe compound $A_2$ in the tumor cells and non-tumor cells in example 5. Hela cells and HEK293 cells were incubated with 44 μL of $A_2$-DMSO (4.0 μM) for 60 min in 5% $CO_2$ at 37° C. The representative areas were selected and imaged with oil-immersion objective lens (100×). The resulting images are representative of replicate experiments (n=3). The images were recorded with the emission in the range of 500-550 nm.

The Labeling Experiment of Probe Compound A₂ for Tumor Tissues and Non-Tumor Tissues Tumor tissue sections and non-tumor tissues sections of mice' lungs were soaked in the compound A₂ PBS solution (10 μM), respectively. After 30 min, take out the section, mounting, safekeeping, the fluorescence images were obtained by two-photon spectral confocal multiphoton microscope. The imaging results indicated that there were strong fluorescence signals in the tumor tissue sections of mice' lungs, but there was no any fluorescence signals in the non-tumor tissue sections of mice' lungs. FIG. 4(a) is confocal image of tumor tissue sections after adding probe A₂, FIG. 4(b) is confocal image of non-tumor tissue sections of mice' lungs after adding probe A₂. The images were recorded with the emission in the range of 500-550 nm.

Example 6

Water Solubility Experiment of Probe Compound A₂

Figure 5:
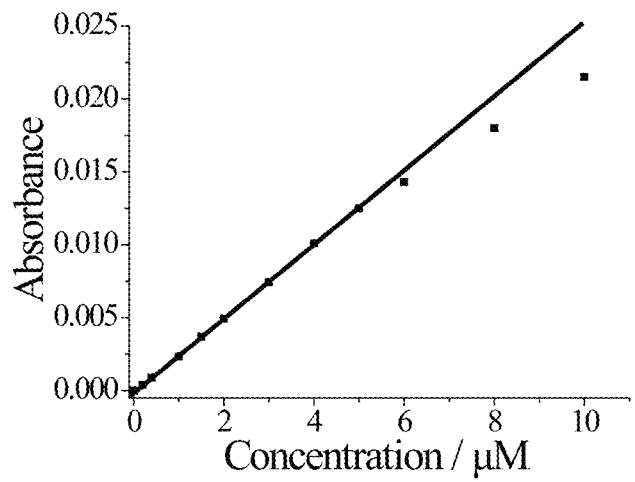
FIG. 5 is the characterization result of water solubility of fluorescent probe compound $A_2$ in example 6. The absorbance of different concentrations of compound $A_2$ solution at maximum absorption wavelength was detected. The results are representative value from replicate experiments (n=3).

The compound A₂ in the mention above example 4 was added into the water, and the absorbance of different concentration compound A₂ at maximum absorption wavelength was detected. The experiment results indicated that the absorbance still not skewed when the concentration of compound A₂ was 5 μM, that is, the water solubility of compound A₂ was 5 μM. FIG. 5 is the absorbance of different concentration compound A₂ at maximum absorption wavelength. The experiment instrument is Agilent 8453 U-V spectrophotometer.

Example 7

The synthesis of fluorescent probe $A_3$

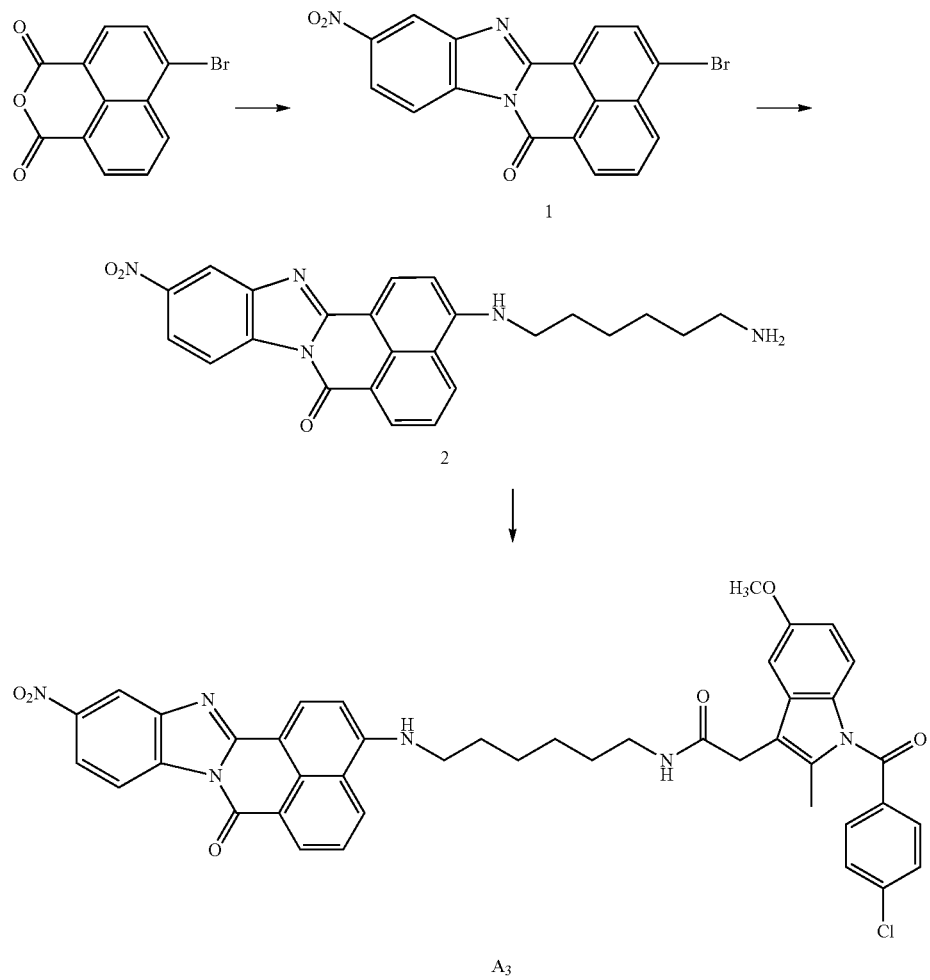

(1) The synthesis of intermediate 1:

20 mmol of 4-bromo-1,8-naphthalic anhydride and 25 mmol of 4-nitro-o-phenylenediamine were added into a round-bottom flask containing 10 mL acetic acid under nitrogen protection, the mixture was heated to reflux for 3 h at 105° C. Then the solution was poured to cooled water and filtrated. The yellow solid powder was collected to obtain the intermediate 1 in a yield of 87%.

(2) The Synthesis of Intermediate 2:

20 mmol of intermediate 1 and 25 mmol of hexamethylenediamine were added into a round-bottom flask containing 20 ml ethylene glycol monomethylether under nitrogen protection, the mixture was heated to reflux for 4 h at 125° C., then the solution was poured into cooled water and filtrated. The residue was purified by silica gel column chromatography, affording intermediate 2 as a red solid powder in a yield of 54%.

(3) The Synthesis of $A_3$ 20 mmol of intermediate 2, 25 mmol of indomethacin, 25 mmol of 1-(3-dimethylaminopropyl)-3-ethylcarbodiimide (EDC) and small amount of 4-methylpyridine were added into in anhydrous methylene chloride and the solution was stirred at room temperature under nitrogen for 24 h. The solvent was removed by vacuum distillation and residue was purified by silica gel column chromatography, affording $A_3$ as a hyacinth solid in a yield of 84%. $^1$H NMR (400 MHz, DMSO) δ 8.99 (d, J=7.2 Hz, 1H), 8.69 (d, J=8.3 Hz, 1H), 8.43 (d, J=7.2 Hz, 1H), 8.25 (d, J=8.5 Hz, 1H), 8.19 (d, J=6.3 Hz, 1H), 8.03 (s, 1H), 7.85 (d, J=4.6 Hz, 1H), 7.72 (d, J=3.5 Hz, 2H), 7.64 (dt, J=20.8, 6.4 Hz, 5H), 7.12 (d, J=2.4 Hz, 1H), 6.91 (d, J=9.0 Hz, 1H), 6.72 (d, J=8.6 Hz, 1H), 6.68 (dd, J=9.0, 2.5 Hz, 1H), 4.22 (s, 1H), 3.48 (s, 2H), 3.37–3.12 (m, 16H), 3.08 (d, J=6.1 Hz, 2H), 2.51 (d, J=1.6 Hz, 6H), 2.22 (s, 3H), 1.71–1.57 (m, 3H), 1.37 (ddd, J=24.7, 14.6, 6.8 Hz, 8H), 1.23 (s, 1H)○

Example 8

Solvent Effects of Probe Compound $A_3$

Figure 6:
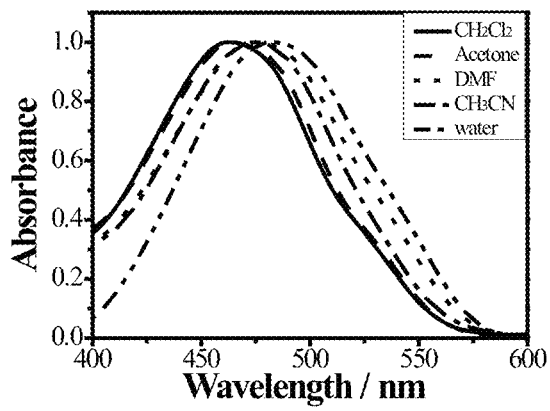
FIG. 6 is the characterization result of solvents effect of fluorescence compound $A_3$ in example 8. The compound $A_3$ was added to the DMSO or THF and the U-V absorption spectra (a) and fluorescence emission spectra (b) of $A_3$ in different solutions are detected.
Figure 6:
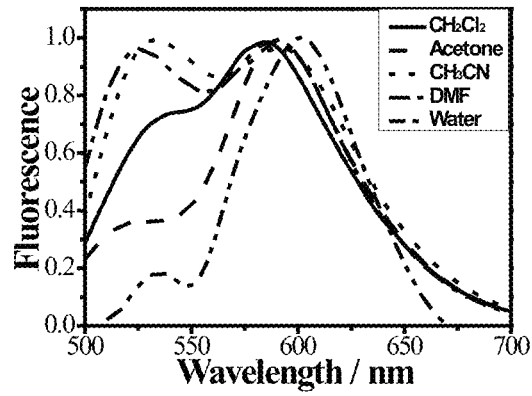

The compound $A_3$, which was synthesized in the example 7, was added into the different solvent (methanol, ethanol, acetone, acetonitrile, dioxane, dimethyl sulfoxide, tetrahydrofuran, N,N-dimethyl formamide, water and so on), and the absorption spectra and fluorescence emission spectra were measured. The detected results indicated that the maximum absorption wavelength occurs corresponding displacement in absorption spectra with the change of the solvent polarity, at the same time, the maximum emission wavelength have corresponding displacement in fluorescence emission spectra. FIG. 6(a) is the U-V absorption spectra of compound $A_3$ in different solvent, FIG. 6(b) is the fluorescence emission spectra of compound $A_3$ in different solvent. The experiment instrument is Agilent 8453 U-V spectrophotometer and Agilent Cary Eclipse fluorescence spectrophotometer.

Example 9

The Detection Experiment of the Two-Photon Cross Section (δ) of $A_3$

The two-photon cross section (δ) of $A_3$ was determined by using femto second (fs) fluorescence measurement technique. The probe compound $A_3$, which was synthesized in the example 7 was dissolved in methanol, ethanol, acetone, acetonitrile, dioxane, dimethyl sulfoxide, tetrahydrofuran, N,N-dimethyl formamide, water and so on, respectively, at concentrations of $1.0 \times 10^{-4}$ M and then the two-photon cross section (δ) was measured by using fluorescein-sodium hydroxide solution (pH=11) as reference solution. The value of two-photon cross section (δ) was obtained by using calculation formula of 2.2.

Figure 7:
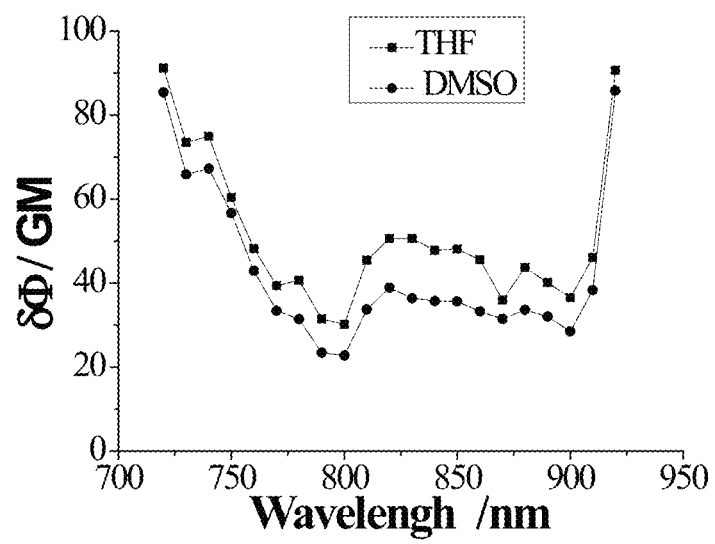
FIG. 7 is the measurement result of two-photon cross section of fluorescent probe compound $A_3$ in different solvents in example 9. The determination solvent is dimethyl sulfoxide (DMSO) and tetrahydrofuran. The method for determine the two-photon cross section (δ) is femtosecond (fs) fluorescence measurement technique. The reference solution is fluorescein-sodium hydroxide solution (pH=11), the concentration of $A_3$ solutions were $1 \times 10^{-4}$ M, the width of laser pulse is 70 fs, repetition frequency is 80 MHz, the average output power is 1.5 W (780 nm), tunable wavelength range is at 700-980 nm, the wavelength of laser was adjusted to the need wavelength in the experiment.

The effective two-photon cross section (δΦ) in different solution and at different wavelength was shown in FIG. 7. The excitation source of two-photon fluorescence spectra is a mode-locked titanium-sapphire laser, the width of laser pulse is 70 fs, repetition frequency is 80 MHz, the average output power is 1.5 W (780 nm), tunable wavelength range is at 700-980 nm, the wavelength of laser was adjusted to the need wavelength in the experiment.

Example 10

The synthesis of fluorescent probe $A_4$

1) The Synthesis of Intermediate 1
33 mmol of acenaphthequinone and 180 mmol of liquid bromine were stirred and slowly heat up to 65° C. and reacted for 3 h at 65° C. The reaction solution was poured to 300 ml of cooled water containing a little $H_2SO_4$, a yellow solid was generated and the solution was showed deep yellow color. The reaction mixture was heated to dislodge liquid bromine and HBr untile the solution changed into colorless from deep yellow color, then the solution was filtrated and the filter cake was washed until the filtrate was neutral and dried to obtain the intermediate 1 in a yield of 90%. M.p.236-238° C.β

(2) The Synthesis of Intermediate 2
20 mmol of intermediate 1 and 25 mmol of o-phenylenediamine was added into a round-bottom flask containing 10 mL acetic acid under nitrogen protection, the mixture was stirred and refluxed for 6 h at 100° C., then the solution was poured to cooled water and filtrated. The yellow solid powder was collected to obtain the intermediate 2 in a yield of 79%.

(3) The Synthesis of Intermediate 3
20 mmol of intermediate 2 and 25 mmol of hexamethylenediamine were added into a round-bottom flask containing 20 ml ethylene glycol monomethylether under nitrogen protection, the mixture was heated to reflux for 6 h at 125° C., then the solution was poured to cooled water and filtrated. The residue was purified by silica gel column chromatography, affording intermediate 3 as a yellow solid in a yield of 66%.

(4) The Synthesis of $A_4$
20 mmol of intermediate 3, 30 mmol of indomethacin, 25 mmol of 1-(3-dimethylaminopropyl)-3-ethylcarbodiimide (EDC), and small amount of 4-methylpyridine were added into in anhydrous methylene chloride and the solution was stirred at room temperature under nitrogen for 25 h. The solvent was removed by vacuum distillation and residue was purified by silica gel column chromatography, affording $A_4$ as a yellow solid in a yield of 74%. $^1$H NMR (400 MHz, DMSO) δ 8.86 (d, J=7.9 Hz, 2H) 8.69 (d, J=8.3 Hz, 1H), 8.43 (d, J=7.2 Hz, 1H), 8.25 (d, J=8.5 Hz, 1H), 8.17 (d, J=6.3 Hz, 2H), 8.03 (s, 1H), 7.72 (d, J=3.5 Hz, 2H), 7.64 (dt, J=20.8, 6.4 Hz, 5H), 7.12 (d, J=2.4 Hz, 1H), 6.91 (d, J=9.0 Hz, 1H), 6.72 (d, J=8.6 Hz, 1H), 6.68 (dd, J=9.0, 2.5 Hz, 1H), 4.22 (s, 1H), 3.48 (s, 2H), 3.37-3.12 (m, 16H), 3.08 (d, J=6.1 Hz, 2H), 2.51 (d, J=1.6 Hz, 6H), 2.22 (s, 3H), 1.71-1.57 (m, 3H), 1.37 (ddd, J=24.7, 14.6, 6.8 Hz, 8H), 1.23 (s, 1H)○

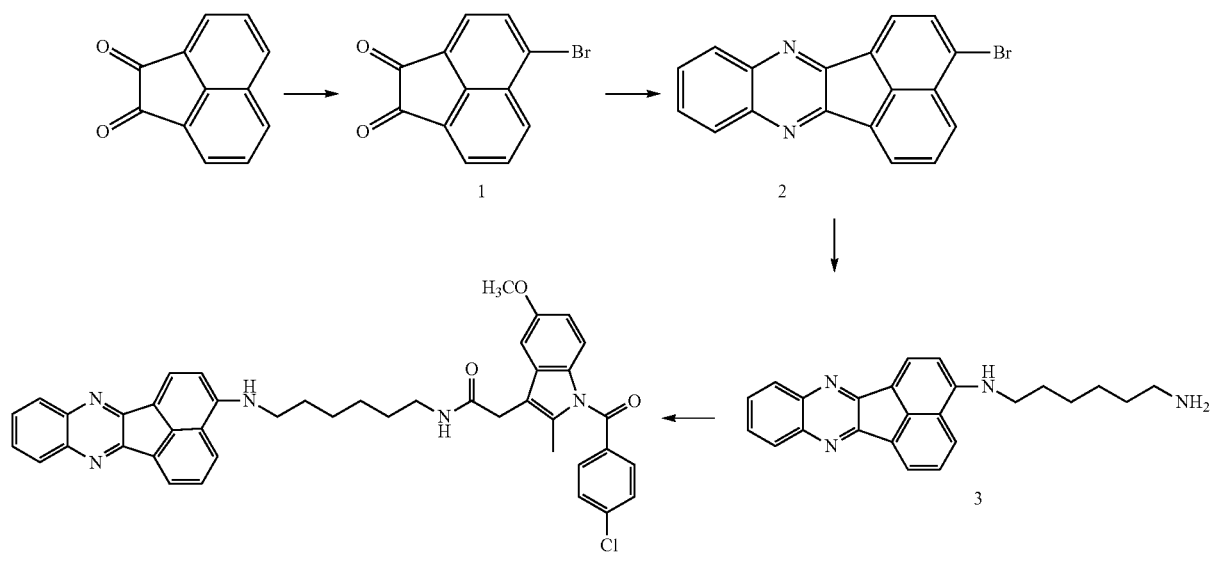

Example 11

Figure 8:
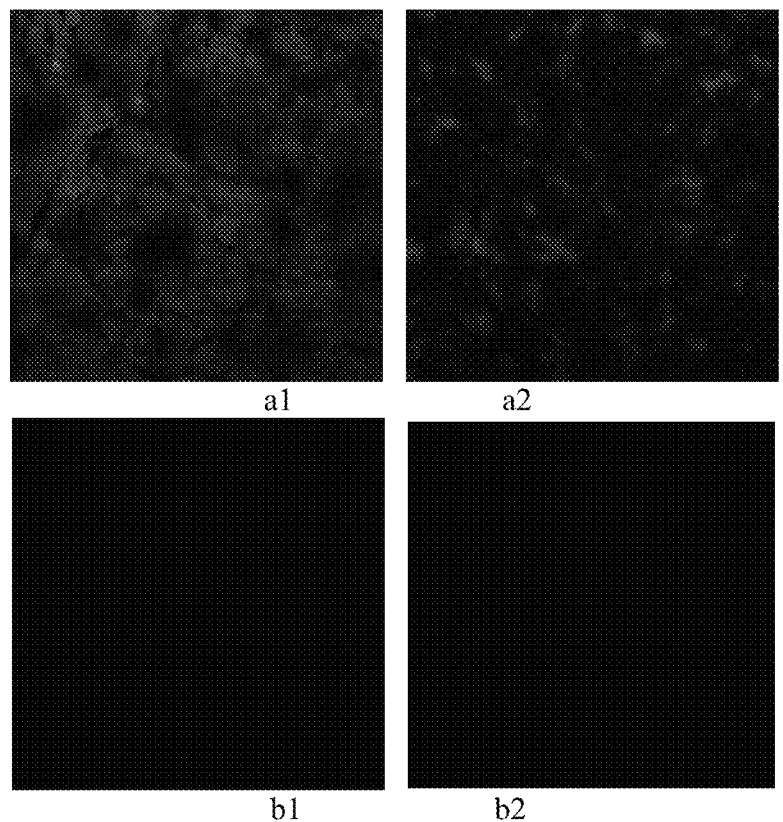
FIG. 8 is the two-photon fluorescent imaging of fluorescent probe compound $A_4$ for the tumor tissues and non-tumor tissues of mice' lungs in example 11. The sections of tumor tissues and non-tumor tissues of mice' lungs were incubated with 4 μL of $A_4$ (10.0 μM). The representative areas were selected and imaged with oil-immersion objective lens (100×). The resulting images are representative of replicate experiments (n=3).

The Labeling Experiment of Probe Compound $A_4$ for Tumor Tissues and Non-Tumor Tissues Tumor tissue sections and non-tumor tissues sections of mice' lungs were soaked in the compound $A_4$ PBS solution (10 μM), respectively. After 30 min, take out the section, mounting, safekeeping, the fluorescence images were obtained by two-photon spectral confocal multiphoton microscope. The imaging results indicated that there were strong fluorescence signals in the tumor tissue sections of mice' lungs, but there was no any fluorescence signals in the non-tumor tissue sections of mice' lungs. FIGS. 8(a1) and 8(a2) are confocal image of tumor tissue sections after adding probe $A_4$, FIGS. 8(b1) and 8(b2) are confocal image of non-tumor tissue sections of mice' lungs after adding probe $A_4$. The images were recorded with the emission in the range of 500-550 nm.

Example 12

Water Solubility Experiment of Probe Compound $A_4$

Figure 9:
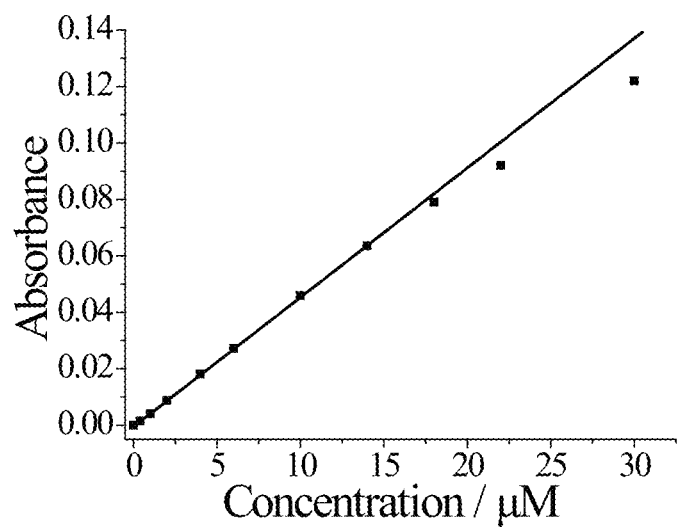
FIG. 9 is the characterization result of water solubility of fluorescent probe compound $A_4$ in example 12. The absorbance of different concentrations of compound $A_4$ solution at maximum absorption wavelength was detected. The results are representative value from replicate experiments (n=3).

The compound $A_4$ mentioned above was added into the water, and the absorbance of different concentration compound $A_4$ at maximum absorption wavelength was detected. The experiment results indicated that the absorbance still not skewed when the concentration of compound $A_4$ was 24 μM, that is, the water solubility of compound $A_4$ was 24 μM. FIG. 9 is the absorbance of different concentration compound $A_4$ at maximum absorption wavelength. The experiment instrument is Agilent 8453 U-V spectrophotometer.

Example 13

The synthesis of fluorescent probe $A_5$

The synthesis of intermediate 1

33 mmol of acenaphthequinone and 180 mmol of liquid bromine were stirred and slowly heat up to 65° C. and reacted for 3 h at 65° C. The reaction solution was poured to 300 ml of cooled water containing a little $H_2SO_4$, a yellow solid was generated and the solution was showed deep yellow color. The reaction mixture was heated to dislodge liquid bromine and HBr until the solution changed into colorless from deep yellow color. Then the reaction solution was filtrated and the filter cake was washed until the filtrate was neutral and dried to obtain the intermediate 1 in a yield of 90%. M.p.236-238° C.

(2) The Synthesis of Intermediate 2

20 mmol of intermediate 1 and 25 mmol of o-phenylenediamine was added into a round-bottom flask containing 10 mL acetic acid under nitrogen protection, the mixture was stirred and refluxed for 5 h at 100° C., then the solution was poured to cooled water and filtrated. The red solid powder was collected to obtain the intermediate 2 in a yield of 83%.

(3) The Synthesis of Intermediate 3

20 mmol of intermediate 2 and 25 mmol of hexamethylenediamine were added into a round-bottom flask containing 20 ml ethylene glycol monomethylether under nitrogen protection, the mixture was heated to reflux for 5.5 h at 125° C., then the solution was poured to cooled water and filtrated. The residue was purified by silica gel column chromatography, affording intermediate 3 as orange red solid powder in a yield of 72%.

(4) The Synthesis of $A_4$ 20 mmol of intermediate 3, 30 mmol of indomethacin, 25 mmol of 1-(3-dimethylaminopropyl)-3-ethylcarbodiimide (EDC), and small amount of 4-methylpyridine were added into in anhydrous methylene chloride and the solution was stirred at room temperature under nitrogen for 25 h. The solvent was removed by vacuum distillation and residue was purified by silica gel column chromatography, affording $A_5$ as a orange red solid in a yield of 69%. $^1$H NMR (400 MHz, DMSO) δ 8.86 (d, J=7.9 Hz, 1H) 8.69 (d, J=8.3 Hz, 1H), 8.43 (d, J=7.2 Hz, 1H), 8.25 (d, J=8.5 Hz, 1H), 8.23 (d, J=6.9 Hz, 1H), 8.18 (d, J=6.3 Hz, 1H), 8.03 (s, 1H), 7.72 (d, J=3.5 Hz,

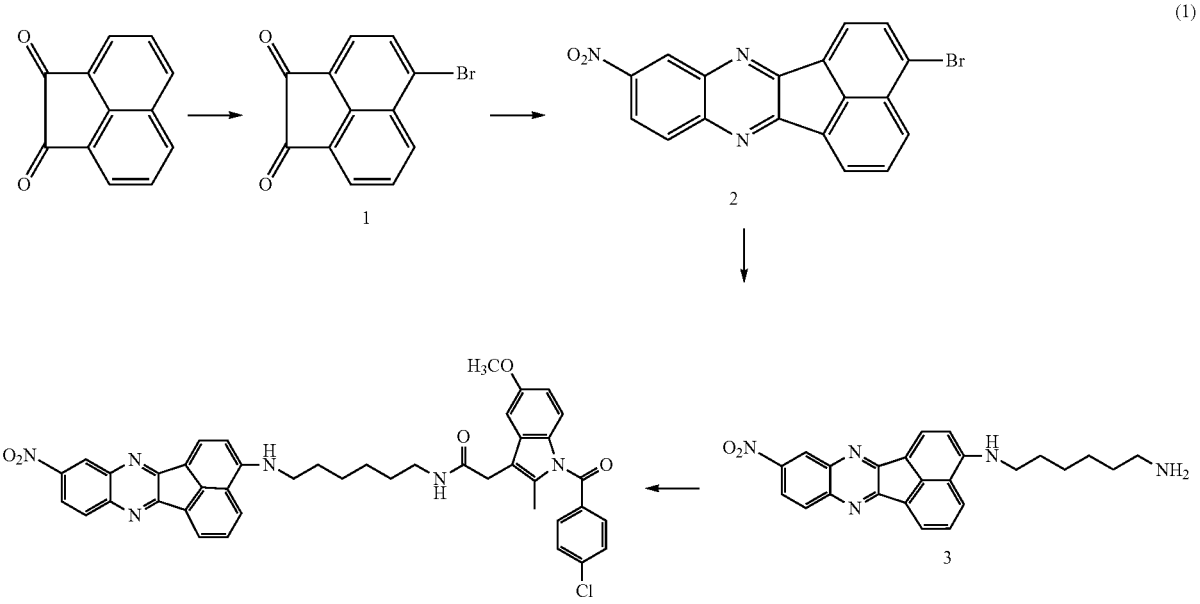

(1)

2H), 7.64 (dt, J=20.8, 6.4 Hz, 5H), 7.12 (d, J=2.4 Hz, 1H), 6.91 (d, J=9.0 Hz, 1H), 6.72 (d, J=8.6 Hz, 1H), 6.68 (dd, J=9.0, 2.5 Hz, 1H), 4.22 (s, 1H), 3.48 (s, 2H), 3.37–3.12 (m, 16H), 3.08 (d, J=6.1 Hz, 2H), 2.51 (d, J=1.6 Hz, 6H), 2.22 (s, 3H), 1.71–1.57 (m, 3H), 1.37 (ddd, J=24.7, 14.6, 6.8 Hz, 8H), 1.23 (s, 1H)○

Example 14

Figure 10:
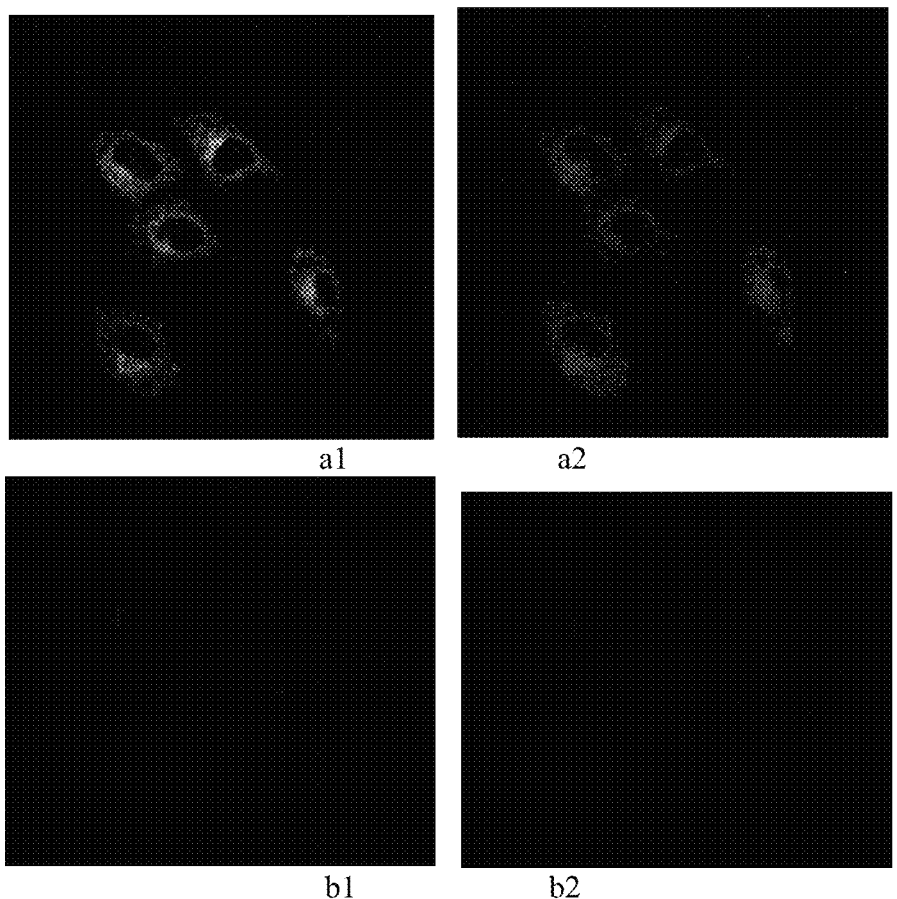
FIG. 10 is two-photon fluorescent imaging of fluorescent probe compound $A_2$ in the tumor cells and non-tumor cells in example 14. Hela cells and HEK293 cells were incubated with 4 μL of $A_5$-DMSO (4.0 μM) for 60 min in 5% $CO_2$ at 37° C. The representative areas were selected and imaged with oil-immersion objective lens (100×). The resulting images are representative of replicate experiments (n=3).

The Labeling Experiment of Probe Compound $A_5$ for Cancer Cells and Non-Cancer Cells Compound $A_5$ was used, which was synthesized in the example 13. 4 μL of compound $A_5$-DMSO solution (4 μM) was added into HeLa and HEK 293 cells, respectively. HeLa and HEK 293 cells with probe $A_5$ were cultured for 60 min in 5% $CO_2$ at 37° C. Then, they were washed with phosphate-buffered saline 5 min×3. After that, the fresh medium was added into every cell. The fluorescence imaging was obtained with a two-photon spectral confocal multiphoton microscope. The representative areas were selected and imaged three times with oil-immersion objective lens (100×). The imaging results indicated that there were strong fluorescence signals in HeLa cells, but there were no any fluorescence signal in HEK 293 cells. FIGS. 10(a1) and 10(a2) are confocal images of HeLa cell after adding probe $A_5$, FIGS. 10(b1) and 10(b2) are confocal images of HEK 293 cell after adding probe $A_5$. The images of FIG. 10(a1) and FIG. 10(b1) were recorded with the emission in the range of 500-550 nm. The images of FIG. 10(a2) and FIG. 10(b2) were recorded with the emission in the range of 500-550 nm.

Example 15

Figure 11:
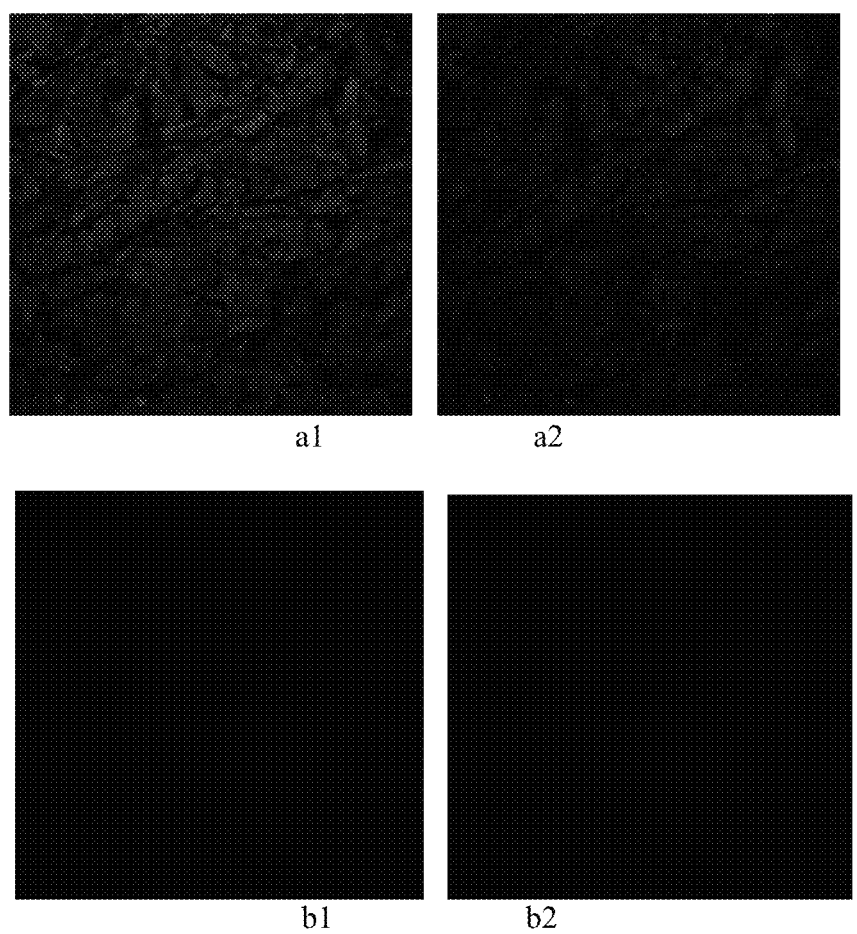
FIG. 11 is two-photon fluorescent imaging of fluorescent probe compound $A_5$ for the tumor tissues and non-tumor tissues of mice' lungs in example 15. The sections of tumor tissues and non-tumor tissues of mice' lungs were incubated with 4 μL of $A_4$ (10.0 μM). The representative areas were selected and imaged with oil-immersion objective lens (100×). The resulting images are representative of replicate experiments (n=3).

The Labeling Experiment of Probe Compound $A_5$ for Tumor Tissues and Non-Tumor Tissues Tumor tissue sections and non-tumor tissues sections of mice' lungs were soaked in the compound $A_5$ PBS solution (10 μM), respectively. After 30 min, take out the section, mounting, safekeeping, the fluorescence images were obtained by two-photon spectral confocal multiphoton microscope. The imaging results indicated that there were strong fluorescence signals in the tumor tissue sections of mice' lungs, but there was no any fluorescence signals in the non-tumor tissue sections of mice' lungs. FIGS. 11(a1) and 11(a2) are confocal image of tumor tissue sections after adding probe $A_5$, FIGS. 11(b1) and 11(b2) are confocal image of non-tumor tissue sections of mice' lungs after adding probe $A_5$. The images of FIG. 11(a1) and FIG. 11(b1) were recorded with the emission in the range of 500-550 nm. The images of FIG. 11(a2) and FIG. 11(b2) were recorded with the emission in the range of 570-650 nm.

Example 16

The synthesis of fluorescent probe $A_6$

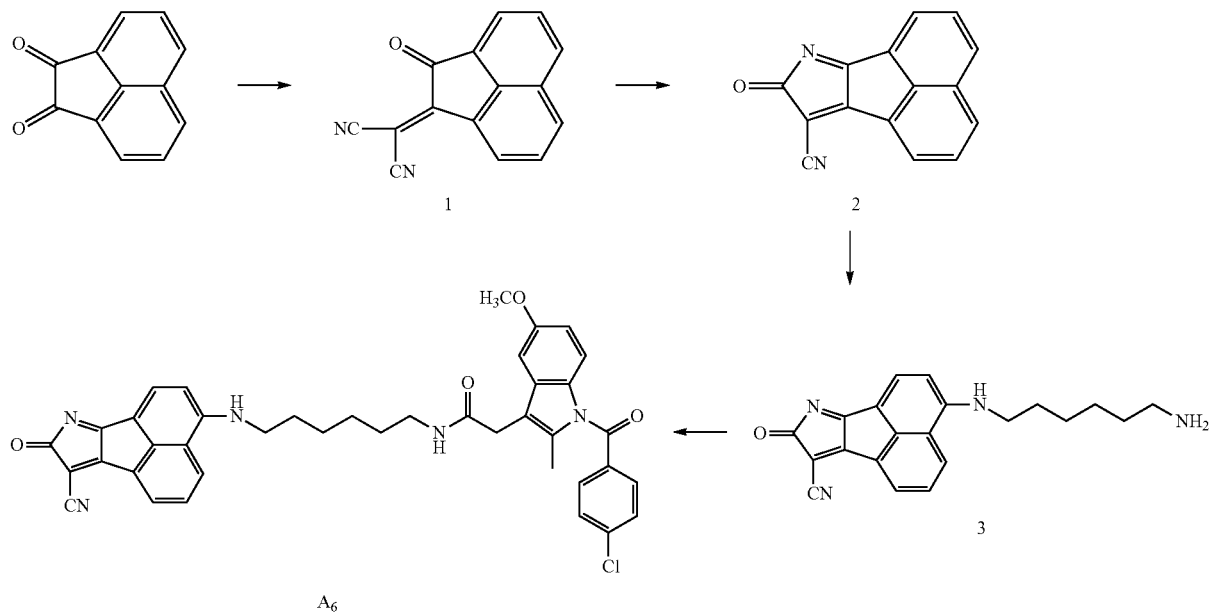

$A_6$ (1) The Synthesis of Intermediate 1

0.5 g of acenaphthequinone and 0.2 g of malononitrile were dissolved in 50 ml of $CH_2Cl_2$, and was directly purified by silica gel column chromatography using a $CH_2C_{12}$ as the eluent. The fraction with an Rf value of 0.8 was collected and evaporated to remove the $CH_2Cl_2$, affording intermediate 1 as orange red solid in a yield of 97%.

(2) The Synthesis of Intermediate 2

1.0 g of intermediate 1 and 0.2 g of $K_2CO_3$ were added into 20 ml of acetonitrile, and the reaction mixture was heated to reflux, a large amount of brown precipitate(crystal) was appeared after several minutes. After cooling, the precipitate was filtered and washed with water to remove the $K_2CO_3$ and dried to obtain the intermediate 2. The yield was greater than 93%.

(3) The Synthesis of Intermediate 3

20 mmol of intermediate 2 and 25 mmol of hexamethyl-enediamine were added into a round-bottom flask containing 20 ml of acetonitrile under nitrogen protection, the mixture was stirred at room temperature for 1 h. After removing the solvent by vacuum distillation, the residue was purified by silica gel column chromatography. The fraction with an Rf value of 0.25 was collected and evaporated to remove the solvent, affording the pure intermediate 3 in a yield of 73%.

(4) The Synthesis of $A_6$ 20 mmol of intermediate 3, 20 mmol of indomethacin, 25 mmol of 1-(3-dimethylaminopropyl)-3-ethylcarbodiimide (EDC), and small amount of 4-methylpyridine were added into in anhydrous methylene chloride and the solution was stirred at room temperature for 25 h. The solvent was removed by vacuum distillation and the residue was purified by silica gel column chromatography, affording $A_6$ as a red solid in a yield of 69%. $^1$H NMR (400 MHz, DMSO) δ 8.95 (d, J=7.6 Hz, 1H), 8.58 (d, J=7.2 Hz, 1H), 7.98 (d, J=8.8 Hz, 1H), 7.88 (t, J=7.8 Hz, 1H), 7.72 (d, J=3.5 Hz, 2H), 7.64 (dt, J=20.8, 6.4 Hz, 5H), 7.12 (d, J=2.4 Hz, 1H), 7.03 (d, J=9.2 Hz, 1H), 6.91 (d, J=9.0 Hz, 1H), 6.72 (d, J=8.6 Hz, 1H), 6.68 (dd, J=9.0, 2.5 Hz, 1H), 4.22 (s, 1H), 3.48 (s, 2H), 3.37–3.12 (m, 16H), 3.08 (d, J=6.1 Hz, 2H), 2.51 (d, J=1.6 Hz, 6H), 2.22 (s, 3H), 1.71–1.57 (m, 3H), 1.37 (ddd, J=24.7, 14.6, 6.8 Hz, 8H), 1.23 (s, 1H)○

Example 17

Solvent effects of probe compound $A_6$

Figure 12:
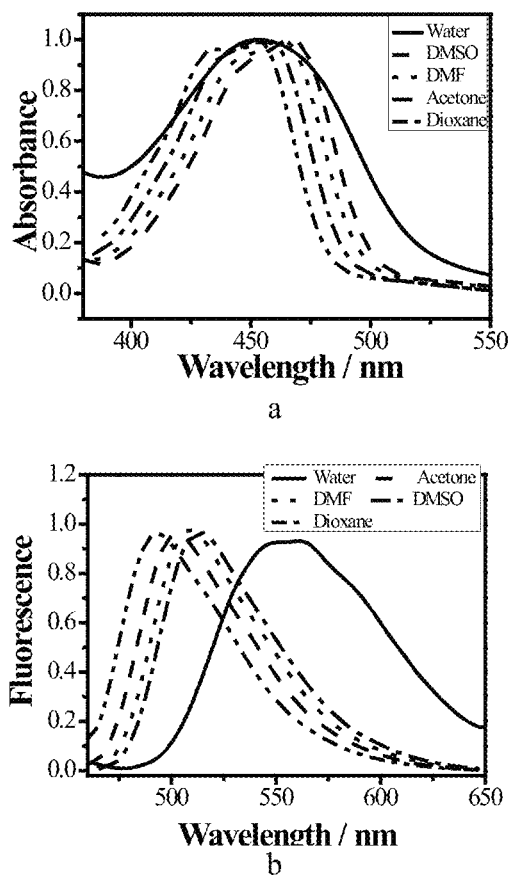
FIG. 12 is the characterization result of solvent effect of fluorescent compound $A_6$ in example 17. The determination solvent is DMSO. The U-V absorption spectra (a) and fluorescence emission spectra (b) of $A_6$ in the different solvents were detected.

The compound $A_6$, which was synthesized in the example 16, was added into the different solvent (methanol, ethanol, acetone, acetonitrile, dioxane, dimethyl sulfoxide, tetrahydrofuran, N,N-dimethyl formamide, water and so on), and the absorption spectra and fluorescence emission spectra were measured. The detected results indicated that the maximum absorption wavelength occurs corresponding displacement in absorption spectra with the change of the solvent polarity, at the same time, the maximum emission wavelength have corresponding displacement in fluorescence emission spectra. FIG. 12(a) is the U-V absorption spectra of compound $A_6$ in different solvent, FIG. 12(b) is the fluorescence emission spectra of compound $A_6$ in different solvent. The experiment instrument is Agilent 8453 U-V spectrophotometer and Agilent Cary Eclipse fluorescence spectrophotometer.

Example 18

The Detection Experiment of the Two-Photon Cross Section (δ) of $A_6$

Figure 13:
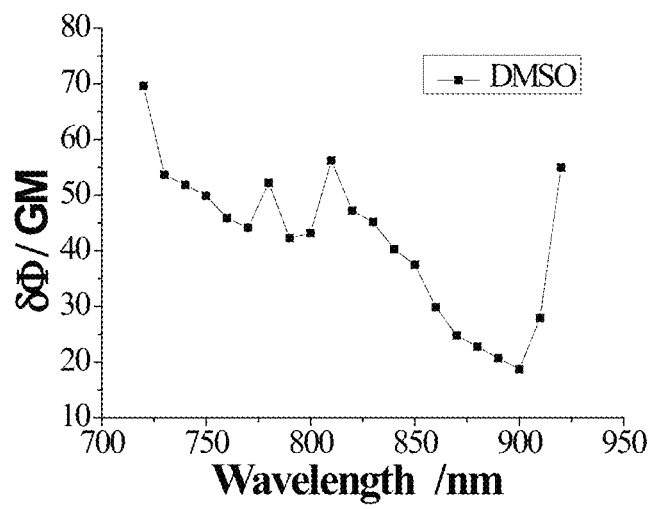
FIG. 13 is the measurement data of two-photon cross section of fluorescent probe compound $A_6$ in different solvents in example 18. The determination solvent is dimethyl sulfoxide (DMSO) and tetrahydrofuran. The method for determine the two-photon cross section (δ) is femto second (fs) two-photon induced fluorescence measurement technique. The reference solution is fluorescein-sodium hydroxide solution (pH=11), the concentrations of $A_3$ solution were $1\times10^{-4}$ M, the width of laser pulse is 70 fs, repetition frequency is 80 MHz, the average output power is 1.5 W (780 nm), tunable wavelength range is at 700-980 nm, the wavelength of laser was adjusted to the need wavelength in the experiment.

The two-photon cross section (δ) of $A_6$ was determined by using femto second (fs) fluorescence measurement technique. The probe compound $A_6$, which was synthesized in the example 16 was dissolved in methanol, ethanol, acetone, acetonitrile, dimethyl sulfoxide, tetrahydrofuran, N,N-dimethyl formamide, water and so on, respectively, at concentrations of $1.0\times10^{-4}$ M and then the two-photon cross section (δ) was measured by using fluorescein-sodium hydroxide solution (pH=11) as reference solution. The value of two-photon cross section (δ) was obtained by using calculation formula of 2.2. The effective two-photon cross section (δΦ) in different solution and at different wavelength was shown in FIG. 13. The excitation source of two-photon fluorescence spectra is a mode-locked titanium-sapphire laser, the width of laser pulse is 70 fs, repetition frequency is 80 MHz, the average output power is 1.5 W (780 nm), tunable wavelength range is at 700-980 nm, the wavelength of laser was adjusted to the need wavelength in the experiment.

The above content is further explained about invention combining with optimization of concrete implementation way, but concrete implementation methods were restricted in this explanation. About the technical staffs in this field of technology, some simple deduction or replace which were made according this invention, should be regarded as fall within the scope of the present invention to protect. The compounds which were reported in this invention can be used as fluorescence dyes, but not only be used as fluorescence dyes. About the technical staffs in this field of technology, some simple ratiocinations which were made according the similar mechanism of this invention, should be regarded as fall within the scope of the present invention to protect.

The invention claimed is:

1. A naphthalene-based two-photon fluorescent probe of formula I:

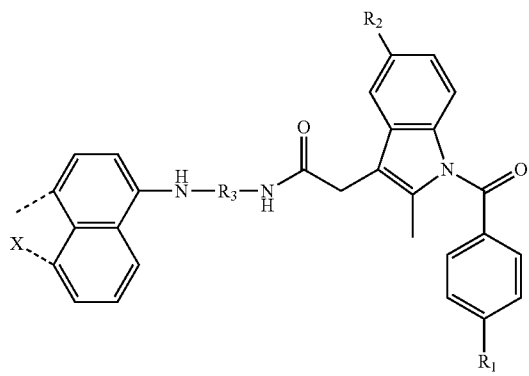

wherein:

X is selected from the group consisting of $X_1$, $X_2$, $X_3$ and $X_4$; wherein X is connected to the fused benzene rings in formula I through bonds represented by dotted lines;

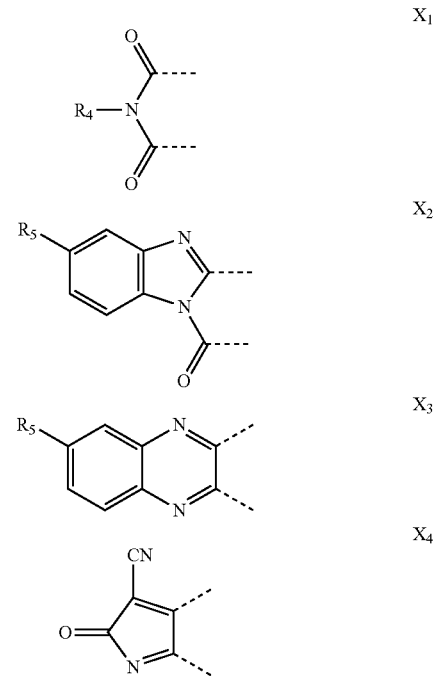

$R_1$ and $R_2$ are each independently selected from the group consisting of —$OCH_3$, —$OCOCH_3$ and halogen;

$R_3$ is selected from the group consisting of —$CH_2$—, —$(CH_2)_2$—, —$(CH_2)_3$—, —$(CH_2)_4$—, —$(CH_2)_5$—, —$(CH_2)_6$—, —$(CH_2)_7$— and —$(CH_2)_8$—;

$R_4$ is selected from the group consisting of $C_{1-6}$ alkyl, $HOCH_2$—, $HO(CH_2)_2$—, $HO(CH_2)_3$—, $HO(CH_2)_4$—, $HO(CH_2)_5$— and $HO(CH_2)_6$—; and $R_5$ is selected from the group consisting of —H, —CN, —COOH, —$NH_2$, —$NO_2$, —OH and —SH.

2. The naphthalene-based two-photon fluorescent probe according to claim 1, wherein $R_1$ and $R_2$ are each independently selected from the group consisting of —$OCH_3$ and halogen.

3. The naphthalene-based two-photon fluorescent probe according to claim 1, wherein $R_3$ is selected from the group consisting of —(CH$_2$)$_5$— and —(CH$_2$)$_6$—.

4. The naphthalene-based two-photon fluorescent probe according to claim 1, wherein $R_4$ is selected from $C_{1-4}$ alkyl.

5. The naphthalene-based two-photon fluorescent probe according to claim 1, wherein $R_5$ is selected from the group consisting of —H, —CN, —COOH and —NO$_2$.

6. The naphthalene-based two-photon fluorescent probe according to claim 1, selected from the compounds consisting of $A_1$, $A_2$, $A_3$, $A_4$, $A_5$ and $A_6$

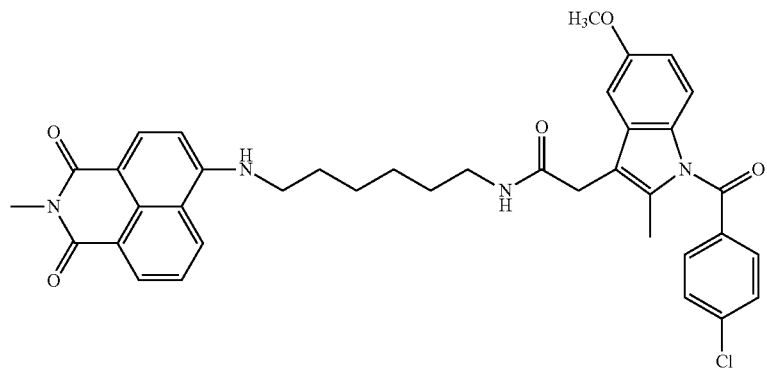

$A_1$

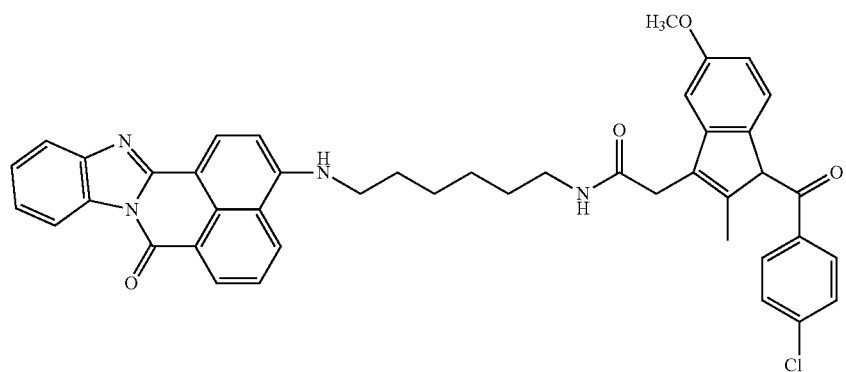

$A_2$

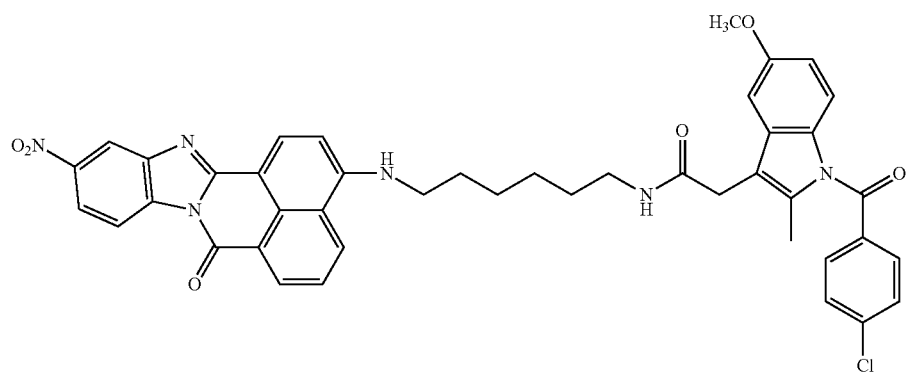

$A_3$

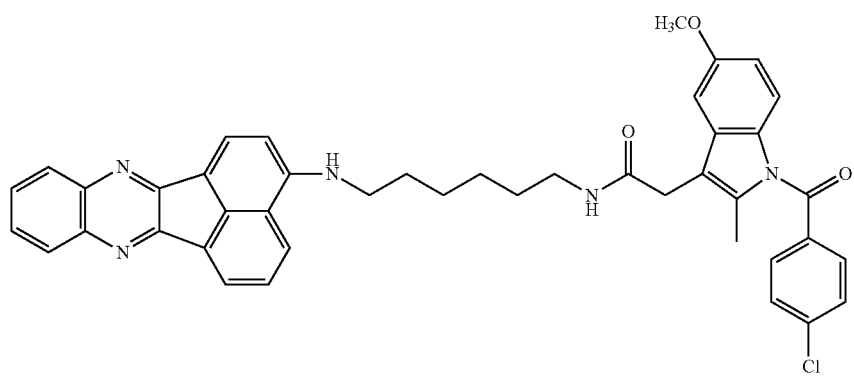

$A_4$

-continued

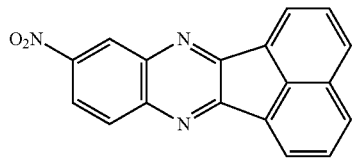
A5

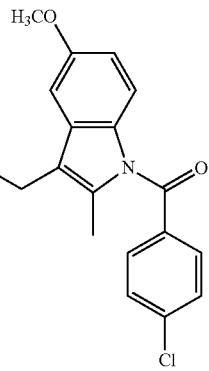

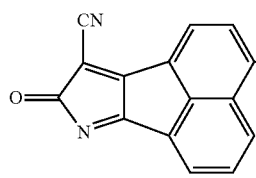
A6

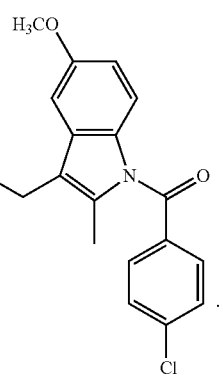

7. A method for synthesizing one or more naphthalene-based two-photon fluorescent probes according to claim 1, comprising:
   1) synthesizing one or more compounds selecting from the group consisting of compounds V, VI, VII, and VIII, wherein compound V is synthesized by reacting 4-bromo-1,8-naphthalic anhydride with $R_4$—$NH_3$ at a mole ratio between 4-bromo-1,8-naphthalic anhydride and $R_4$—$NH_3$ of 1:1-1:5

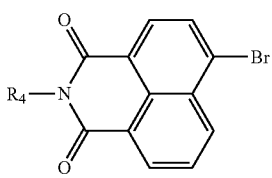
V at 70-150° C. for 1-12 hours in a reaction solvent selected from a group consisting of dichloromethane, ethanol, ethyl acetate, acetic acid, and mixtures thereof;
wherein compound VI is synthesized by reacting 4-bromo-1,8-naphthalic anhydride with compound i at a mole ratio between 4-bromo-1,8-naphthalic anhydride and compound i of 1:1-1:5

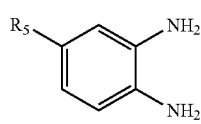
i

-continued

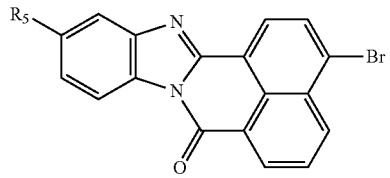
VI at 70-150° C. for 1-12 hours in a reaction solvent selected from a group consisting of dichloromethane, ethanol, ethyl acetate, acetic acid, and mixtures thereof;
wherein compound VII is synthesized by reacting 4-bromoacenaphthenequinone with compound i at a mole ratio between 4-bromoacenaphthenequinone and compound i of 1:1-1:5

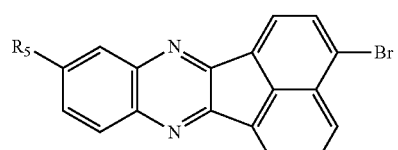
VII at 70-150° C. for 1-12 hours in a reaction solvent selected from a group consisting of dichloromethane, ethanol, ethyl acetate, acetic acid, and mixtures thereof;
wherein compound VIII is synthesized by reacting acenaphthenequinone with malononitrile and dimethyl sulfoxide at a mole ratio of acenaphthenequinone to malononitrile to dimethyl sulfoxide of 1:1:5

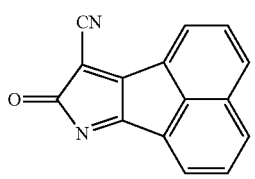

at room temperature for 0.5 hours, and then at 70-180° C. for 4-12 hours in a reaction solvent selected from the group consisting of dimethyl sulfoxide, tetrahydrofuran, an aqueous solution of dimethyl sulfoxide, and an aqueous solution of tetrahydrofuran, and mixtures thereof;

2) synthesizing one or more of compounds selected from the group consisting of compounds IX, X, XI and XII, wherein compounds IX, X, XI, and XII are respectively synthesized by reacting $NH_2R_3NH_2$ with compounds V, VI, VII and VIII, respectively, at a mole ratio of 1:1-1:2.5 at 100-175° C. for 1-7 hours in a reaction solvent selected from the group consisting of ethanol, 2-methoxyethanol, or a mixture thereof;

3) synthesizing one or more compounds of formula I, wherein the compound of formula I is synthesized by reacting the compound ii with one selected from the group consisting of compounds IX, X, XI and XII at a mole ratio of 1:1-1:3 at 0-100° C. for 12-48 hours in a reaction solvent selected from the group consisting of methylene chloride, ethanol, ethyl acetate or mixtures thereof in the presence of an organic base and 4-dimethyl amino pyridine.

8. The method according to the claim 7, wherein the aqueous solution of dimethyl sulfoxide or the aqueous solution of tetrahydrofuran has a mole ratio between water and dimethyl sulfoxide or tetrahydrofuran of 1:1-1:2.5.

9. A method for labeling a biological sample, comprising:
obtaining a naphthalene-based two-photon fluorescent probe of claim 1; and
staining the biological sample with the naphthalene-based two-photon fluorescent probe.

10. The method according to the claim 9, wherein the biological sample is tumor tissues or tumor cells.

\* \* \* \* \*